US007267979B2

(12) United States Patent
Yadav

(10) Patent No.: US 7,267,979 B2
(45) Date of Patent: Sep. 11, 2007

(54) METHOD OF CONTROLLING GENE SILENCING USING SITE SPECIFIC RECOMBINATION

(75) Inventor: Narendra S. Yadav, Chadds Ford, PA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 567 days.

(21) Appl. No.: 10/611,748

(22) Filed: Jun. 30, 2003

(65) Prior Publication Data

US 2006/0143737 A1 Jun. 29, 2006

Related U.S. Application Data

(60) Provisional application No. 60/393,250, filed on Jul. 1, 2002.

(51) Int. Cl.
*C12N 15/82* (2006.01)
*C12N 5/10* (2006.01)
*A01H 5/00* (2006.01)

(52) U.S. Cl. .................................. 435/320.1; 435/419
(58) Field of Classification Search ..................... None
See application file for complete search history.

(56) References Cited

U.S. PATENT DOCUMENTS 6,077,992 A    6/2000    Yadav
6,110,736 A    8/2000    Hodges et al.

FOREIGN PATENT DOCUMENTS

| WO | WO91/09957    | 7/1991  |
| WO | WO93/01283 A1 | 1/1993  |
| WO | WO97/37012    | 10/1997 |
| WO | WO 00/17365 A2| 3/2000  |
| WO | WO 01/36595 A2| 5/2001  |

OTHER PUBLICATIONS

Fire, A., RNA-triggered gene silencing, Trends Genet. 15(9): pp. 358-383, 1999.
Sharp, P.A., RNAI and double-strand RNA, Genes Dev., vol. 13: pp. 139-141, 1999.
Sharp et al., RNA Interference, Science, 287, 5482, 2431-3, 2000.
Waterhouse et al., Gene silencing as an adaptive defence against viruses, Nature, 411:834-842, Jun. 14, 2001.
Vaucheret et al., Transcriptional gene silencing in plants: targets, inducers and regulators, TRENDS in Genetics 17(1): pp. 29-35, 2001.
Okamoto et al., Silencing of transposable elements in plants, TRENDS in Plant Sci. 6(11): 527-534, 2001.
Pruss, et al., Plant Viral Synergism: The P{otyviral Genome Encodes a Broad-Range Pathogenicity Enhancer that Transactivates Replication of Heterologous Viruses, Plant Cell 9: pp. 859-888, 1997.
Anandalakshmi et al., A viral suppressor of gene silencing in plants, Proc. Natl. Acad. Sci. USA, 95,(22): 13079-84, 1998.

Brigneti, G. et al., Viral pathogenicity determinants are suppressors of transgene silencing in *Nicotiana benthamiana*, EMBO J., 17(22): 6739-46, 1998.
Kasschau, K. D. and J. C. Carrington, A Counterdefensive Strategy of Plant Viruses: suppressionof Postranscriptional Gene Silencing, Cell, 95(4): 481-70, 1998.
Smith et al., Total silencing by intron-spliced hairpin RNAs, Nature 407: 319, 2000.
De Buck et al., Transgene silencing of invertedly repeated transgenes is released upon deletion of one of the transgenes involved, Plant Mol. Biol. 46: 433, 2001.
Hulvagner et al., A Cellular Function for the RNA-Interference Enzyme Dicer in the Maturation of the let-7 Small Temporal RNA, Science 293: 834, 2001.
Odell et al., Seed Specific Gene Activation Mediated by the Cre/lox Site-Specific Recombination System, Plant Physiol. 106: 447-458, 1994.
Russel et al., Directed excision of a transgene from the plant genome, Mol. Gen. Genet. 234: 49-59, 1992.
Craig, The mechanism of Conservative Site-Specific Recombination, Annu. Rev. Genet. 22: 77-105, 1998.
Odell et al., Use of site-specific recombination systems in plants. Homologous Recomb. Gene Silencing Plants, 1994, pp. 219-270, Paszkowski, Jerzy, ed. Kluwer: Dordrecht, Germany.
Zubko et al., Intrachromosomal recombination between attP regions as a tool to remove selectable marker genes from tobacco transgenes, Nature, Biotechnology, 18: 442, 2000.
Groth et al., A phage integrase directs efficient site-specific integration in human cells, Proc. Natl. Acad. Sci. USA 97: 5995, 2000.
Chromosome Engineering in *Saccharomyces cerevisiae* by Using a Site-Specific Recombination System of a Yeast Plasmid, H. Matsuzaki et al., J. Bacteriology, 172, 610, 1990.
Onouchi et al., Operation of an efficient site-specific recombination system of *Zygosaccharomyces rouxii* in tobacco cells, Nucleic Acid Res., 19: 6373-1991.
Ambros, Dicing Up RNAs, Science 293: 811-813, Aug. 3, 2001.
Vance et al., RNA Silencing in Plants—Defense and Counterdefense, Science 292: 2277, 2001.
Knight et al., A Role for the Rnase III Enzyme DCR-1 in RNA Interference and Germ Line Development in *Caenorhabditis elegans*, Science vol. 293, Sep. 21, 2001.

(Continued)

*Primary Examiner*—Ashwin Mehta

(57) ABSTRACT

This invention relates to methods of controlling gene silencing using site-specific recombination. A variety of constructs are provided which are useful for conditional or regulated gene silencing in plants, comprising a suite of constitutive, inducible, tissue-specific or developmental stage-specific promoters operably linked to target sequences (TS). Recombinase inversion or excision yields double-stranded TS RNA, which thereby functions to trigger endogenous gene silencing mechanisms. By matching promoters, responsive to various inducers, plant tissues or plant developmental states with the recombinase systems, transcriptional stop fragments or introns and target sequences, gene silencing of virtually any target sequence may be modulated at any plant development stage or in any plant generation. This is especially useful, when genes responsible for gene silencing are down-regulated to permit expression of particular transgenes at levels greater than permitted when gene silencing is activated.

17 Claims, 5 Drawing Sheets

OTHER PUBLICATIONS

Odell et al., Site-directed recombination in the genome of transgenic tobacco, Mol. Gen. Genet. 1990, vol. 223-pp. 369-378.

Russell et al., Tissue-specific expression in transgenic maize of four endosperm promoters from maize and rice, Transgenic Research 6, pp. 157-168, 1997.

Lyznik et al., FLP-mediated recombination of FRT sites in the maize genome, Nucleic Acids Research, 1998, vol. 24, No. 19, pp. 3784-3789.

Holtorf et al., Comparison of different constitutive and inducible promoters for the overexpression of transgenes in *Arabidopsis thaliana*, Plant Molecular Biology vol. 29, pp. 637-648, 1995.

Dalmay et al., AN RNA-DependentRNA Polymerase Gene in *Arabidopsis* is Required for Posttranscriptional Gene Silencing mediated by a Transgene but Not by a Virus, Cell, vol. 101, 543-553, May 26, 2000.

Lloyd et al., Functional expression of the yeast FLP/FRT site-specific recombination system in *Nicotiana tabacum*, Mol. Gen. Genet. 1994, vol. 242: pp. 653-657.

SEQUENCE LISTING

<160> NUMBER OF SEQ ID NOS: 21

<210> SEQ ID NO 1
<211> LENGTH: 30
<212> TYPE: DNA
<213> ORGANISM: Artificial Sequence
<220> FEATURE:
<223> OTHER INFORMATION: P314 upper primer

<400> SEQUENCE: 1
cccaagcttt cctttgcccc ggagattaca                               30

<210> SEQ ID NO 2
<211> LENGTH: 37
<212> TYPE: DNA
<213> ORGANISM: Artificial Sequence
<220> FEATURE:
<223> OTHER INFORMATION: P315 lower primer

<400> SEQUENCE: 2
ttccatgact agtcaggatc ctgcagaatt cataact                       37

<210> SEQ ID NO 3
<211> LENGTH: 38
<212> TYPE: DNA
<213> ORGANISM: Artificial Sequence
<220> FEATURE:
<223> OTHER INFORMATION: P316 upper primer

<400> SEQUENCE: 3
aattctgcag gatcctgact agtcatggaa gacgccaa                      38

<210> SEQ ID NO 4
<211> LENGTH: 37
<212> TYPE: DNA
<213> ORGANISM: Artificial Sequence
<220> FEATURE:
<223> OTHER INFORMATION: P317 lower primer

<400> SEQUENCE: 4
ataaagccta ggtacccggg catgcgagaa tctcacg                       37

<210> SEQ ID NO 5
<211> LENGTH: 44
<212> TYPE: DNA
<213> ORGANISM: Artificial Sequence
<220> FEATURE:
<223> OTHER INFORMATION: P318 upper primer

<400> SEQUENCE: 5
tctcgcatgc ccgggtacct aggctttatg agctgcaaac acac               44

<210> SEQ ID NO 6
<211> LENGTH: 37
<212> TYPE: DNA
<213> ORGANISM: Artificial Sequence
<220> FEATURE:
<223> OTHER INFORMATION: P319 lower primer

<400> SEQUENCE: 6
ccgagctcgg caactatttt tatgtatgca agagtca                       37

<210> SEQ ID NO 7
<211> LENGTH: 57

```
<212> TYPE: DNA
<213> ORGANISM: Artificial Sequence
<220> FEATURE:
<223> OTHER INFORMATION: P330 upper primer

<400> SEQUENCE: 7
ccgtcgacat aacttcgtat agcatacatt atacgaagtt ataagctttc ctttgcc        57

<210> SEQ ID NO 8
<211> LENGTH: 51
<212> TYPE: DNA
<213> ORGANISM: Artificial Sequence
<220> FEATURE:
<223> OTHER INFORMATION: P320 lower primer

<400> SEQUENCE: 8
ttccatgact agtcaggatc ctgcagaatt cctcgagcgt gtcctctcca a              51

<210> SEQ ID NO 9
<211> LENGTH: 34
<212> TYPE: DNA
<213> ORGANISM: Artificial Sequence
<220> FEATURE:
<223> OTHER INFORMATION: 34 bp Lox P site

<400> SEQUENCE: 9
ataacttcgt atagcataca ttatacgaag ttat                                 34

<210> SEQ ID NO 10
<211> LENGTH: 34
<212> TYPE: DNA
<213> ORGANISM: Artificial Sequence
<220> FEATURE:
<223> OTHER INFORMATION: 34 bp Lox P* sequence

<400> SEQUENCE: 10
ataacttcgt ataatgtatg ctatacgaag ttat                                 34

<210> SEQ ID NO 11
<211> LENGTH: 25
<212> TYPE: DNA
<213> ORGANISM: Artificial Sequence
<220> FEATURE:
<223> OTHER INFORMATION: 25 bp polylinker sequence

<400> SEQUENCE: 11
gaattctgca ggatcctgac tagtc                                           25

<210> SEQ ID NO 12
<211> LENGTH: 15
<212> TYPE: DNA
<213> ORGANISM: Artificial Sequence
<220> FEATURE:
<223> OTHER INFORMATION: 15 bp polylinker sequence

<400> SEQUENCE: 12
cccgggtacc taggc                                                      15

<210> SEQ ID NO 13
<211> LENGTH: 42
<212> TYPE: DNA
<213> ORGANISM: Artificial Sequence
<220> FEATURE:
<223> OTHER INFORMATION: P321 lower primer

<400> SEQUENCE: 13
```
gaagcagaaa caaaccttac ccgggcatgc gagaatctca cg    42

<210> SEQ ID NO 14
<211> LENGTH: 30
<212> TYPE: DNA
<213> ORGANISM: Artificial Sequence
<220> FEATURE:
<223> OTHER INFORMATION: P322 upper primer

<400> SEQUENCE: 14
gcatgcccgg gtaaggtttg tttctgcttc    30

<210> SEQ ID NO 15
<211> LENGTH: 48
<212> TYPE: DNA
<213> ORGANISM: Artificial Sequence
<220> FEATURE:
<223> OTHER INFORMATION: P323 lower primer

<400> SEQUENCE: 15
ttcgtatagc atacattata cgaagttatc aattgctata tactacat    48

<210> SEQ ID NO 16
<211> LENGTH: 48
<212> TYPE: DNA
<213> ORGANISM: Artificial Sequence
<220> FEATURE:
<223> OTHER INFORMATION: P324 upper primer

<400> SEQUENCE: 16
ttcgtataat gtatgctata cgaagttatc ttttctgtag tttataag    48

<210> SEQ ID NO 17
<211> LENGTH: 33
<212> TYPE: DNA
<213> ORGANISM: Artificial Sequence
<220> FEATURE:
<223> OTHER INFORMATION: P325 lower primer

<400> SEQUENCE: 17
ctcgcatgcc cgggtaacct aggcatcacc atg    33

<210> SEQ ID NO 18
<211> LENGTH: 33
<212> TYPE: DNA
<213> ORGANISM: Artificial Sequence
<220> FEATURE:
<223> OTHER INFORMATION: P326 upper primer

<400> SEQUENCE: 18
gtgatgccta ggttacccgg gcatgcgaga atc    33

<210> SEQ ID NO 19
<211> LENGTH: 35
<212> TYPE: DNA
<213> ORGANISM: Artificial Sequence
<220> FEATURE:
<223> OTHER INFORMATION: P327 lower primer

<400> SEQUENCE: 19
taaagcagga ctctagacca tggaagacgc caaaa    35

<210> SEQ ID NO 20
<211> LENGTH: 24
<212> TYPE: DNA
<213> ORGANISM: Artificial Sequence -continued

```
<220> FEATURE:
<223> OTHER INFORMATION: 24 bp polylinker sequence

<400> SEQUENCE: 20
gaattctgca ggatcctgac tagt                                              24

<210> SEQ ID NO 21
<211> LENGTH: 10
<212> TYPE: DNA
<213> ORGANISM: Artificial Sequence
<220> FEATURE:
<223> OTHER INFORMATION: 10 bp linker

<400> SEQUENCE: 21
gttacccggg                                                              10
```

METHOD OF CONTROLLING GENE SILENCING USING SITE SPECIFIC RECOMBINATION

This application claims the benefit of U.S. Provisional Application 60/393,250, filed Jul. 1, 2002.

FIELD OF INVENTION

The present invention relates to the field of molecular biology and the genetic transformation of organisms with foreign gene fragments. More particularly, the invention relates to methods of controlling gene silencing using site-specific recombination.

BACKGROUND OF THE INVENTION

The advent of genetic engineering holds many promises. The transformation of crop plants with new transgenes encoding desirable traits promises improved crop yields and qualities. The ability to utilize plants as platforms for the bioproduction of materials (e.g., a multiplicity of monomers and polymers currently only available by chemical synthetic means) promises processes with lower production costs, higher qualities, and reduced environmental impact. The transformation of animals with new transgenes encoding desirable traits promises novel research or commercial applications, such as improved disease resistance. However, despite the tantalizing promises of genetic engineering, scientists must overcome two significant, yet related, challenges. First, it is necessary to develop techniques that overcome the consequences of gene silencing, whereby expression of the introduced foreign gene is dramatically suppressed; and second, a mechanism for silencing undesirable endogenous genes must be discovered. Both of these requirements can be achieved by conditional control of gene silencing.

Gene silencing (GS) was first recognized when the following inverse correlation was noted: multiple copies of a transgene were often associated with dramatic inhibition of that transgene's product and any host genes that possessed homology to that transgene. Now, gene silencing is known to occur by a decrease in the steady state levels of mRNA for a specific target gene, where the target gene is an endogenous gene or a transgene and is of chromosomal or viral origin.

Gene silencing is believed to have evolved as a host defense mechanism against foreign DNA elements and viruses, as it appears to be conserved in all eukaryotes and, at least, in one single cell alga. Specifically, recent studies have shown that post-transcriptional gene silencing (PTGS) in plants, RNA interference (RNAi) in worms, flies, and mammals, and quelling in fungi share common steps in gene silencing (Fire, A. *Trends Genet.* 15(9):358-63 (1999); Sharp, P. A. *Genes Dev.,* 13:139-141 (1999); Sharp, P. A. and P. D. Zamore, *Science,* 287(5462): 2431-3 (2000)). In each form of gene silencing, double-stranded RNA (ds RNA) is an efficient trigger for the sequence-specific degradation of its cognate mRNA. Transcription of the promoter resulting in ds RNA can also lead to transcriptional gene silencing (TGS), a second form of gene silencing in plants.

Considerable efforts have focused on understanding the gene silencing phenomenon and mechanism of action in plants. A variety of review articles discuss TGS and PTGS, such as those of Waterhouse, P. M., et al. (*Nature* 411:834-842 (14 Jun. 2001)), Vaucheret, H. and M. Fagard (*TRENDS in Genetics* 17(1):29-35 (2001)), and Okamoto, H. and H. Hirochika (*TRENDS in Plant Sci.* 6(11):527-534 (2001)). The following summary of gene silencing is presented only as an overview.

In plants, gene silencing can be triggered by transgene duplication events (tandem repeat transgene sequences, inverted repeat transgene sequences, or multiple insertions into the chromosome) or when a sequence homologous to the target gene sequence is carried either by an infecting plant virus or by the T-DNA of an infiltrating *Agrobacterium*. Thus, the ds RNA trigger for TGS or PTGS can be either synthesized in vitro and then introduced into a cell; or, it can be made by transcription from a transgene construct in vivo.

Currently, TGS is not as well understood as PTGS. TGS occurs when transcription of the target gene is blocked. The process appears to be meiotically heritable and correlates with DNA template modification manifested by hyper-methylation of promoters of silenced genes or with local changes of chromatin structure. It has been postulated that TGS is a defense system against invasive DNA, such as transposable elements; but, experimental evidence for this hypothesis has not been obtained as of yet.

In contrast, post-transcriptional gene silencing (PTGS) occurs in plants when the target gene is transcribed, but its mRNA is sequence-specifically degraded before it can be translated. Thus, this reduction in mRNA is caused by an increased turnover of target RNA species, in which the transcription level of the corresponding genes remains unaffected. Corresponding gene products are therefore only able to accumulate at very low levels. One specific type of PTGS occurs as virus-induced gene silencing (VIGS), in which the sequence homologous to the target gene sequence is carried by an infecting cytoplasmically replicating plant virus. PTGS can be initiated in a variety of ways, and is thought to underlie the phenomena of co-suppression of endogenous plant genes and depressed expression of transgenes.

One of the most intriguing features of PTGS in transgenic plants is that it operates in a non-cell autonomous manner. A signal of gene silencing can move between cells through plasmodesmata and over long distances through the vascular system, directing sequence-specific degradation of target RNAs. The nature of the signal is unknown; but, based on the specificity of its degradation, it is thought to be mediated by short RNA species corresponding to the target RNA that accumulates in tissues exhibiting PTGS (i.e., RNA approximately 21-25 nucleotides in length). Furthermore, although the exact mechanism by which PTGS operates is yet to be elucidated, it has been discovered that viruses can both initiate and be a target of PTGS. A virus-induced silencing signal could therefore migrate cell-to-cell in advance of the infection front and be transported over long distances through the phloem. The effect of this intercellular signalling would be to potentiate RNA sequence-specific virus resistance in non-infected tissues and, consequently, to delay spread of the virus through the plant.

Evidence of plant viruses having evolved as a counter-defense to PTGS was determined by studies of synergistic viral disease, where co-infection with two heterologous viruses led to much more severe symptoms than did infection with either virus alone. Transgenic plants expressing the 5' proximal region of the tobacco etch potyviral (TEV) genome (i.e., PI/HC-Pro sequence) developed synergistic disease when infected with any of a broad range of plant viruses (Pruss, G., et al. *Plant Cell* 9:859-868 (1997)). This suggested that expression of the PI/HC-Pro sequence interfered with a general antiviral system in plants that permitted viruses to accumulate beyond the normal host-mediated limits. More recently, a plant viral protein (HC-Pro) has been identified that interferes with the induction of PTGS (Anandalakshmi, R. et al. *Proc. Natl. Acad. Sci. USA.,* 95(22): 13079-84 (1998); Brigneti, G. et al. *EMBO J.,* 17(22): 6739-46 (1998); Kasschau, K. D. and J. C. Carrington, *Cell,* 95(4): 461-70 (1998)), further supporting the idea that PTGS may be linked to natural antiviral resistance systems in plants. It was shown that this synergism was due to suppression of a host defense mechanism by the Hc-protease (HcPro) encoded in the potyviral genome (e.g., tobacco vein mottling virus, tobacco etch virus, and potato virus Y). Subsequent studies further established that HcPro was a suppressor of PTGS and provided a link between PTGS and antiviral defense. Thus, suppressors of gene silencing can be used inter alia for improving expression of desirable genes, particularly heterologous genes, in plants (WO 98/44097).

Despite the previous work identifying suppressors of gene silencing, these solutions are limited by the undesirable side effects of many, if not all, suppressors of gene silencing or by mutations in host gene silencing. A significant contribution to the art, therefore, would be the development of a general mechanism whereby conditional manipulation of PTGS or other gene silencing pathways would serve as an effective means for modulating expression of endogenous or foreign target genes. That is, it would be desirable to control when—and in which tissue—the expression of the target sequence is enhanced, decreased, or silenced.

Currently, few methods exist that provide for the conditional manipulation of the gene silencing pathways to silence 1.) specific gene-silencing genes, thereby permitting higher level expression of transgenes that would ordinarily be silenced; and, 2.) undesirable endogenous genes, thereby permitting their down-regulation. Transgenes encoding hairpin or ds RNA have been used to silence target genes (Smith et. al. *Nature* 407:319 (2000); De Buck et. al. *Plant Mol. Biol.* 46:433 (2001)). And, silencing of a gene-silencing gene (i.e., the DICER gene) has also been demonstrated in the art (Hutvagner et. al. *Science* 293:834 (2001)). However, it has not been shown that such silencing can be conditionally activated. Conditional silencing is essential, as constitutive silencing is not desirable when silencing of a target gene is lethal or deleterious to normal growth and development of an organism. Additionally, conditional silencing of a gene involved in gene silencing would permit production of high levels of materials in transgenic plants that normally are susceptible to gene silencing. And further, methods of conditionally silencing the expression of an endogenous or foreign target gene would enable economic production of desired chemicals, monomers, and polymers, with high levels of expression being restricted to transgenic biomass (production tissue) either just prior to, or after, its harvest for extracting the desired product. Thus, regulated ds RNA expression would be desirable for regulated gene silencing of target genes at a specific developmental time or in a specific tissue or generation.

Site-specific recombination [Odell et al., *Plant Physiol.* 106:447-458 (1994); Odell et al., WO 91/09957 (1991); Surin et al WO 97/37012 (1997); Ow et al., WO 93/01283 A1 (1992); Russel et al., *Mol. Gen. Genet.* 234:49-59 (1992); and Hodges et al., U.S. Pat. No. 6,110,736] in plants has been demonstrated. Furthermore, regulated site-specific recombination (SSR) in plants has also been demonstrated in plants using binary expression systems, where one transgenic cassette carries a site-specific recombinase and the other carries the inactive trait. The expression of this trait gene (TG) is blocked by the presence of a 'blocking' or 'STOP' fragment, flanked by the cognate SSR sites, which blocks transcription and/or translation of the TG. Recombinase expression leads to SSR and removal of the "blocking" DNA fragment, thereby permitting transgene activation. This can be regulated to occur in a specific developmental stage of the plant, tissue, or generation (Yadav et al., WO 01/36595 A2; WO 00/17365 A2; U.S. Pat. No. 6,077,992; EP1115870 A2). However, a sitespecific recombination system has never been used as a method to control gene silencing. Thus, the problem to be solved, therefore, is to develop a system for conditionally regulating gene silencing through the implementation of SSR systems, such that target gene expression leads to production of ds RNA which thereby triggers gene silencing.

Applicant has solved the stated problem in the present invention through the development of a method for conditional regulation of gene silencing based on site-specific recombinase systems. These systems comprise a recombinase element (which leads to expression of an active recombinase enzyme) and a gene silencing-recombinase element (which leads to expression of the target sequence as ds RNA).

SUMMARY OF THE INVENTION

The present invention provides methods for the conditional or regulated expression of gene silencing by the application of a site-specific recombinase system. This enables gene silencing to be controlled in a temporal, tissue-specific, and/or generation-specific manner.

Accordingly the invention provides a gene silencing site-specific recombination system comprising:
  a) a first recombinase element having the general structure P1-R, wherein P1 is a first promoter and R is a recombinase coding sequence and 3' region; and
  b) a second gene silencing-recombinase element having the general structure: RS-X-RS*-Y
  wherein:
    i) RS and RS* are oppositely oriented recombinase sites responsive to the recombinase;
    ii) X is a nucleic acid fragment comprising at least one second promoter in a 3' to 5' orientation; and
    iii) Y is a nucleic acid fragment comprising at least one target sequence;

wherein expression of the recombinase results in inversion of the element contained between RS and RS* and transcription of the second gene silencing-recombinase element resulting in the production of double-stranded RNA and silencing of the target gene.

Additionally the invention provides a gene silencing site-specific recombination system comprising:
  a) a first recombinase element having the general structure P1-R, wherein P1 is a first promoter and R is a recombinase coding sequence and 3' region; and
  b) a second gene silencing-recombinase element having the general structure: P2-TS-RS-Z-RS-TS$_{INV}$-polyA;
  wherein:
    a) P2 is a second promoter;
    b) TS is a target sequence;
    c) RS is a recombinase site responsive to the recombinase
    d) Z is a nucleic acid fragment selected from the group consisting of a STOP fragment and an intron;
    e) TS$_{INV}$ is an inverted target sequence whose orientation is from 3'-5'; and
    f) polyA is the 3' region of a gene.

In a preferred embodiment the invention provides a gene silencing site-specific recombination system comprising:
   a) a first recombinase element having the general structure P1-R, wherein P1 is a first promoter and R is a recombinase coding sequence and 3' region; and
   b) a second gene silencing-recombinase element having the general structure: RS-TS$_{INV}$-P2$_{INV}$-RS*-TS$_{INV}$-polyA, wherein:
      i) RS and RS* are opposingly oriented recombinase sites responsive to the recombinase;
      ii) TS$_{INV}$ is an inverted target sequence whose orientation is from 3'-5';
      iii) P2$_{INV}$ is an inverted second promoter whose orientation is from 3'-5'; and
      iv) polyA is the 3' region of a gene;

wherein P1 and P2 are operably linked to their down stream elements and wherein expression of the recombinase results in inversion of the element contained between RS and RS* and transcription of the gene silencing-recombinase element resulting in production of double-stranded RNA and silencing of the target gene.

In similar fashion the invention provides a gene silencing site-specific recombination system comprising:
   a) a first recombinase element having the general structure P1-R, wherein P1 is a first promoter and R is a recombinase coding sequence and 3' region; and
   b) a second gene silencing-recombinase element having the general structure RS-5' Intron-TS$_{INV}$-P2$_{INV}$-RS*-3' Intron-TS$_{INV}$-polyA, wherein:
      (i) RS and RS* are opposingly oriented recombinase sites responsive to the recombinase;
      (ii) 5' Intron is the N-terminal portion of an intron;
      (iii) TS$_{INV}$ is an inverted target sequence and whose orientation is from 3'-5';
      (iv) P2$_{INV}$ is an inverted second promoter whose orientation is from 3'-5';
      (v) 3' Intron is the C-terminal portion of an intron; and
      (vi) polyA is the 3' region of a gene;

wherein P1 and P2 are operably linked to their down stream elements and wherein expression of the recombinase results in inversion of the element contained between RS and RS* and transcription of the gene silencing-recombinase element, resulting in excision of the intron by mRNA splicing and production of double-stranded RNA and silencing of the target gene.

Additionally the invention provides a gene silencing site-specific recombination system comprising:
   a) A recombinase element having the general structure P1-R, wherein P1 is a first promoter and R is a recombinase coding sequence and 3' region; and
   b) A gene silencing-recombinase element having the general structure RS-P2$_{INV}$-RS*-TS-P3$_{INV}$, wherein:
      i) RS and RS* are opposingly oriented recombinase sites responsive to the recombinase;
      ii) P2$_{INV}$ and P3$_{INV}$ are inverted second and third promoters respectively, whose orientation is from 3'-5'; and
      iii) TS is a target sequence;

wherein P1, P2, and P3 are operably linked to their down stream elements and wherein expression of the recombinase results in inversion of the element contained between RS and RS* and transcription of the gene silencing-recombinase element resulting in production of double-stranded RNA silencing the target gene.

In another embodiment the invention provides a gene silencing site-specific recombination system comprising:
   a) A recombinase element having the general structure P1-R, wherein P1 is a first promoter and R is a recombinase coding sequence and 3' region; and
   b) A gene silencing-recombinase element having the general structure P2-TS-RS-STP-RS-TS$_{INV}$-polyA, wherein:
      i) P2 is a second promoter;
      ii) TS is a target sequence;
      iii) RS is a recombinase site responsive to the recombinase;
      iv) STP is a Transcriptional 'STOP' fragment;
      v) TS$_{INV}$ is an inverted target sequence and whose orientation is from 3'-5'; and
      vi) polyA is the 3' region of a gene;

wherein P1 and P2 are operably linked to their down stream elements and wherein expression of the recombinase results in excision of the element contained between RS and transcription of the gene silencing-recombinase element resulting in production of double-stranded RNA silencing the target gene.

In another embodiment the invention provides a gene silencing site-specific recombination system comprising:
   a) A recombinase element having the general structure P1-R, wherein P1 is a first promoter and R is a recombinase coding sequence and 3' region; and
   b) A gene silencing-recombinase element having the general structure P2-TS-5' Intron-RS-STP-RS-3' Intron-TS$_{INV}$-polyA, wherein:
      i) P2 is a second promoter;
      ii) TS is a target sequence;
      iii) 5'Intron is the N-terminal portion of an intron;
      iv) RS is a recombinase site responsive to the recombinase;
      v) STP is a Transcriptional 'STOP' fragment;
      vi) 3'Intron is the C-terminal portion of an intron;
      vii) TS$_{INV}$ is an inverted target sequence whose orientation is from 3'-5'; and
      viii) polyA is the 3' region of a gene;

wherein P1 and P2 are operably linked to their down stream elements and wherein expression of the recombinase results in excision of the element contained between RS and transcription of the gene silencing-recombinase element resulting in excision of the intron by mRNA splicing and production of double-stranded RNA silencing the target gene.

In another aspect the invention provides a method for silencing a target gene, comprising introducing into a plant cell comprising a target gene, a gene silencing construct of the invention wherein expression of the recombinase results in translation of the target sequence and the production of double-stranded target sequence RNA.

Additionally the invention provides a method for expressing conditional gene silencing in a plant comprising:
   A) providing constructs comprising:
      i) a first recombinase element having the general structure P1-R;
      ii) a second gene silencing-recombinase element having a general structure selected from the group consisting of:
         1) RS-P2$_{INV}$-RS-TS-P3$_{INV}$;
         2) RS-TS$_{INV}$-P2$_{INV}$-RS-TS$_{INV}$-polyA;
         3) RS-5' Intron-TS$_{INV}$-P2$_{INV}$-RS-3' Intron-TS$_{INV}$-polyA;
         4) P2-TS-RS-STP-RS-TS$_{INV}$-polyA; or 5) P2-TS-5' Intron-RS-STP-RS-3' Intron-TS$_{INV}$-polyA; wherein:
   a) P1 is a first promoter;
   b) R is a recombinase;
   c) RS is a recombinase site responsive to the recombinase;
   d) P2 and P3 are second and third promoters that have overlapping expression profiles and are either the same or different;
   e) P2$_{INV}$ is an inverted second promoter whose orientation is from 3'-5';
   f) TS is a target sequence optionally having an operably-linked poly A region at the 3' end of each complementary strand;
   g) TS$_{INV}$ is an inverted target sequence whose orientation is from 3'-5';
   h) 5'Intron is the N-terminal portion of an intron;
   i) 3'Intron is the C-terminal portion of an intron;
   j) STP is a Transcriptional 'STOP' fragment; and
   k) polyA is the 3' region of a gene;
wherein P1, P2, P2$_{INV}$, and optionally P3, are operably linked to their down stream elements;

B) providing a first plant having a target gene and comprising the first recombinase element;

C) providing a second plant having a target gene and comprising the second gene silencing-recombinase element; and D) crossing the first and second plants to produce progeny in which expression of the recombinase under the control of P1 promoter inverts or excises the elements between the recombinase sites on the second gene silencing-recombinase element permitting the formation of double-stranded RNA encoding the target sequence to silence the target gene in the plant.

In an alternate embodiment the invention provides a method for effecting systemic gene silencing in a plant comprising:

A) providing constructs comprising:
   i) a first recombinase element having the general structure P1-R;
   ii) a second gene silencing-recombinase element having a general structure selected from the group consisting
      1) RS-P2$_{INV}$-RS-TS-P3$_{INV}$;
      2) RS-TS$_{INV}$-P2$_{INV}$-RS-TS$_{INV}$-polyA;
      3) RS-5' Intron-TS$_{INV}$-P2$_{INV}$-RS-3' Intron-TS$_{INV}$-polyA;
      4) P2-TS-RS-STP-RS-TS$_{INV}$-polyA; or
      5) P2-TS-5' Intron-RS-STP-RS-3' Intron-TS$_{INV}$-polyA;
   iii) a third gene-silencing-mobility element having the general structure P4-TS$_R$;
   wherein:
      a) P1 is a first promoter that is chemically inducible;
      b) R is a recombinase;
      c) RS is a recombinase site responsive to the recombinase;
      d) P2 and P3 are second and third promoters that have overlapping expression profiles and are either the same or different;
      e) P2$_{INV}$ is an inverted second promoter whose orientation is from 3'-5';
      f) TS is a target sequence optionally having an operably-linked poly A region at the 3' end of each complementary strand;
      g) TS$_{INV}$ is an inverted target sequence whose orientation is from 3'-5';
      h) 5'Intron is the N-terminal portion of an intron;
      i) 3'Intron is the C-terminal portion of an intron;
      j) STP is a Transcriptional 'STOP' fragment; and
      k) polyA is the 3' region of a gene;
      l) P4 is a strong constitutive promoter; and
      m) TS$_R$ is redundant target sequence comprising at least a target sequence selected from the group consisting of TS and TS$_{INV}$;
   wherein P1, P2, P2$_{INV}$, optionally P3, and P4 are operably linked to their down stream elements;

B) providing a plant having a target gene and comprising the first recombinase element, the second gene silencing-recombinase element, and the third gene silencing-mobility element; and C) chemically inducing the P1 promoter to cause inversion or excision of the elements between the recombinase sites on the second gene silencing-recombinase element permitting the formation of double-stranded RNA encoding the target sequence to silence the target gene and creation of a mobile gene-silencing signal in the plant for systemic silencing.

BRIEF DESCRIPTION OF FIGURES AND SEQUENCE DESCRIPTIONS

Figure 1:
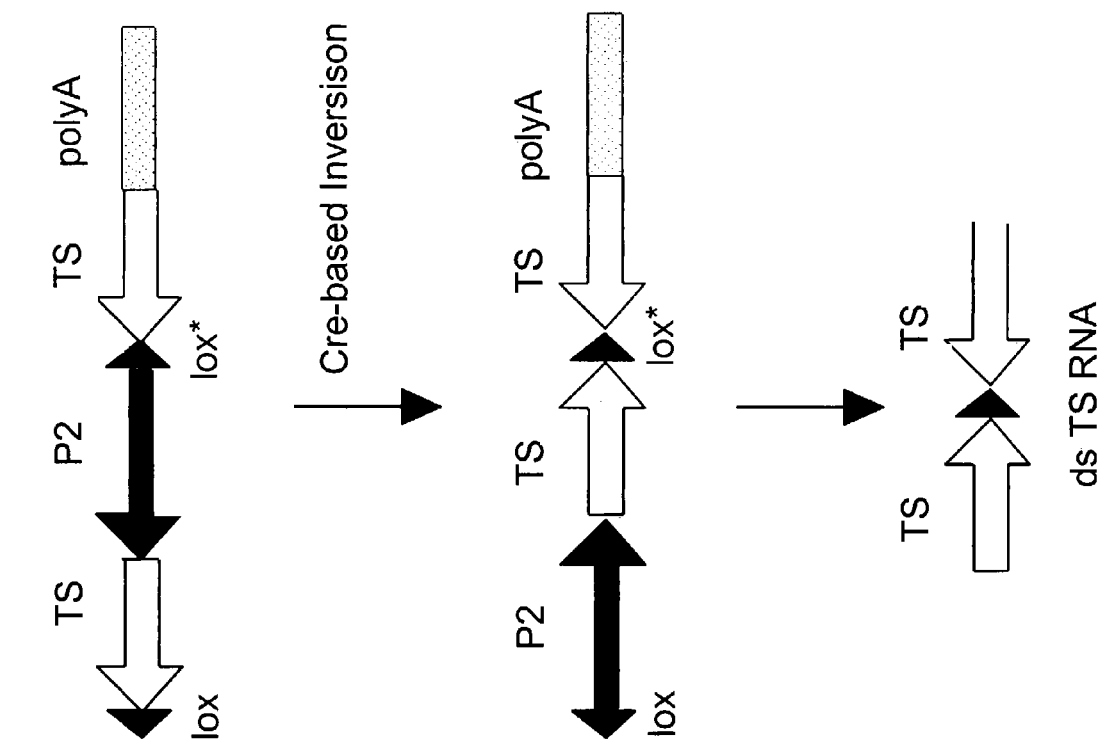
FIG. 1 shows inversion of a promoter and target sequence by sitespecific recombination to produce ds TS RNA (double-stranded target sequence RNA).

The following sequence descriptions and sequence listings attached hereto comply with the rules governing nucleotide and/or amino acid sequence disclosures in patent applications as set forth in 37 C.F.R. §1.821-1.825. The Sequence Descriptions contain the one letter code for nucleotide sequence characters and the three letter codes for amino acids as defined in conformity with the IUPAC-IYUB standards described in *Nucleic Acids Research* 13:3021-3030 (1985) and in the *Biochemical Journal*, 219 (No. 2):345-373 (1984) which are herein incorporated by reference. The symbols and format used for nucleotide and amino acid sequence data comply with the rules set forth in 37 C.F.R. §1.822.

SEQ ID NOs: 1 and 2 are P314 upper primer and P315 lower primer, respectively.

SEQ ID NOs: 3 and 4 are P316 upper primer and P317 lower primer, respectively.

SEQ ID NOs: 5 and 6 are P318 upper primer and P319 lower primer, respectively.

SEQ ID NOs: 7 and 8 are P330 upper primer and P320 lower primer, respectively.

SEQ ID NOs: 9 and 10 are Lox P and LoxP* sites, respectively.

SEQ ID NOs: 11, 12, 20, and 21 are polylinker and linker sequences used in vector construction.

SEQ ID NO: 13 is 321 lower primer.

SEQ ID NOs: 14 and 15 are P322 upper primer and P323 lower primer, respectively.

SEQ ID NOs: 16 and 17 are P324 upper primer and P325 lower primer, respectively.

SEQ ID NOs: 18 and 19 are P326 upper primer and P327 lower primer, respectively.

DETAILED DESCRIPTION OF THE INVENTION

The present invention describes constructs and methods of regulating gene silencing (GS) to thereby modulate the expression of a target gene that is either an endogenous gene or a transgene. This regulation of gene silencing can be achieved by placing expression of a double-stranded (ds) target sequence (TS) RNA (i.e., the "silencing trigger") under the control of an appropriate developmental, tissue-specific, or chemically regulated promoter. Additionally, production of ds TS RNA is regulated by a site-specific recombination (SSR) system. SSR can occur either by 1.) activation of a developmental, tissue-specific, or chemically inducible promoter operably linked to the recombinase enzyme; or 2.) by genetically crossing a line capable of expressing the cognate recombinase to a line carrying the recombination sites and the TS.

Abbreviations and Definitions

The following abbreviations will be used herein:

"GS" is the abbreviation for gene silencing.

"PTGS" is the abbreviation for post-transcriptional gene silencing.

"VIGS" is the abbreviation for virus induced gene silencing.

"TGS" is the abbreviation for transcriptional gene silencing.

"SSR" is the abbreviation for site-specific recombination.

"ds" is the abbreviation for double-stranded.

"TS" is the abbreviation for a target sequence.

"$TS_R$" is the abbreviation for a redundant target sequence.

"polyA" is the abbreviation for polyadenylation signal sequences.

"PCR" is the abbreviation for Polymerase Chain Reaction.

The following terms and definitions shall be used to fully understand the specification and claims.

The term "gene silencing" will refer to the interruption or suppression of the expression of a gene at transcriptional or translational levels. Typically, the phenomenum results such that the mRNA of introduced transgenes and other TSs (and optionally the mRNA from homologous endogenous genes and/or the invading virus RNA that has homology to the transgenes) is degraded. This leads to decreased levels of gene expression (either partial or total reduction); the term should not be taken to require complete "silencing" of expression. The present definition of gene silencing will encompass gene silencing that occurs by "transcriptional gene silencing", "post-transcriptional gene silencing", and "virus-induced gene silencing".

"Transcriptional gene silencing" is a form of silencing where transcription of the gene is blocked. It can be identified by a combination of transcription run-on and Northern analyses.

"Post-transcriptional gene silencing" is silencing of a target sequence caused by the introduction of homologous ds RNA, a transgene, or virus into a cell containing the target sequence. In PTGS, the transcript of the silenced gene is synthesized, but does not accumulate, because of its rapid degradation prior to translation. PTGS can be identified by a combination of transcription run-on and Northern analyses to show that RNA encoded by sense transgenes are degraded after transcription.

"Virus-induced gene silencing" is a specialized form of PTGS that is induced by viruses rather than transgenes.

"RNA interference", or "RNAi", is a term typically used by animal developmental biologists that refers to the introduction of homologous ds RNA to specifically target a gene's product, resulting in null or hypomorphic phenotypes (due to suppression of gene expression). RNAi has arisen from the observation that sense and antisense RNA are equally effective in suppressing specific gene expression. Today, RNAi is often called PTGS.

"Cosuppression" refers to silencing of an endogenous gene caused by the introduction of a transgene or infection by a virus. This term, which can refer to silencing at the post-transcriptional (PTGS) or transcriptional (TGS) level, has been primarily adopted by researchers working with plants.

A "gene silencing site-specific recombination system" will hereinafter refer to a system comprising at least two classes of genetic constructs: a recombinase element containing a site-specific recombinase enzyme; and, a gene silencing-recombinase element that is a substrate for SSR and that comprises a TS to be expressed as ds RNA. Optionally, the gene silencing site-specific recombination system may comprise a third genetic construct: the gene silencing-mobility element. The gene silencing site-specific recombination system will lead to silencing of the target gene.

"Target gene" refers to a gene that is the target of GS and may comprise either transgenes or endogenous genes. Particularly useful target genes will include (but not be limited to): genes conveying a specific phenotype on a plant or plant cell, genes encoding an enzyme of a biosynthetic pathway, genes encoding a storage protein, genes controlling plant development, genes conveying sterility, and hormone biosynthetic genes. Endogenous genes that are useful target genes include genes encoding proteins of the GS apparatus itself, allowing higher expression of any transgene without limitation from its GS. Such host genes involved in GS include qde-1, qde-2, qde-3, rde-1, rde-2, rde-3, rde-4, mut-2, mut-7, ego-1, AGO1, SGS-2/SDE-1, SGS-1, SGS-3, RdRP, and Dicer.

Figure 2:
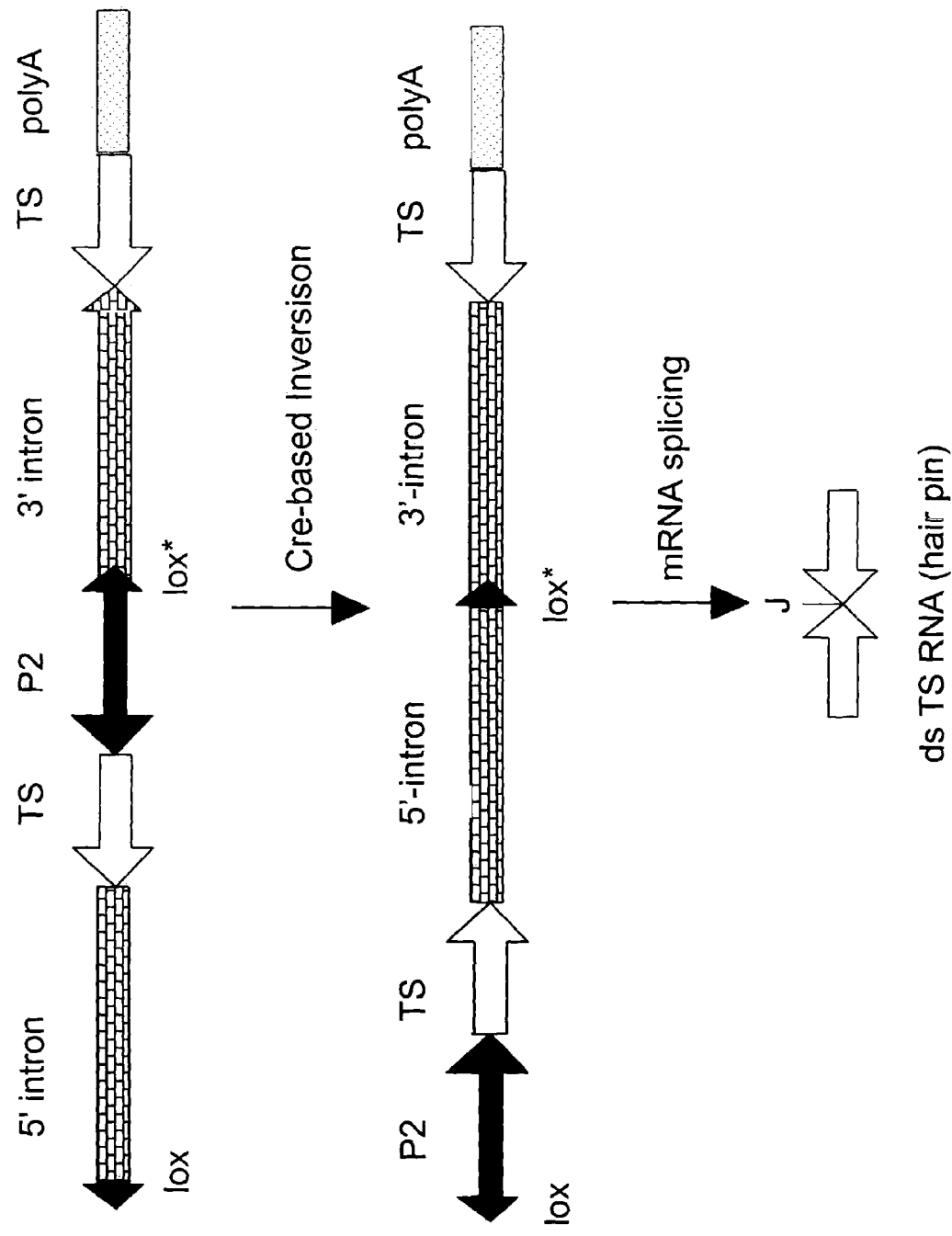
FIG. 2 shows inversion of a promoter, target sequence, and intron by sitespecific recombination to produce ds TS RNA.
Figure 3:
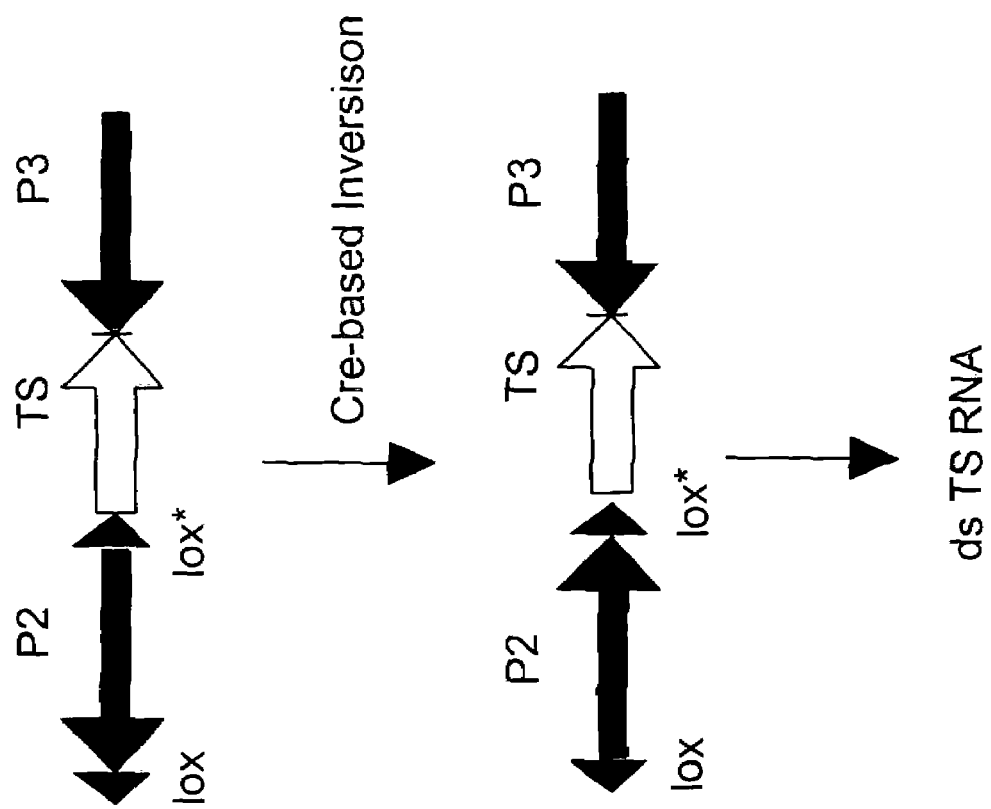
FIG. 3 shows inversion of a promoter by sitespecific recombination to produce ds TS RNA.

"Target sequence" (TS) refers to a sequence of DNA which, when operably-linked to a promoter, is expressed as a ds RNA (ds TS RNA), including hairpin RNA. This ds TS RNA then acts as a "trigger" of GS of the target gene in the host organism. The TS may be homologous to at least one target mRNA expressed by the host organism; thus, the ds RNA is comprised of complementary sequences homologous to the target mRNA(s). For the production of ds RNA, the complementary strands may be transcribed from different promoters (e.g., P2 and P3 in FIG. 3) or from the same promoter (e.g., P2 in FIGS. 1, 2, 4, and 5), such that the ds RNA forms a hairpin structure either with a e.g., Lox P sequence as an intervening loop sequence (FIGS. 1 and 4) or without (FIGS. 2, 3 and 5). Alternatively, the TS may be two complementary sequences which are unrelated to the target gene or any host mRNA but which are in proximity to (either 5' or 3') or are flanking a sequence that is homologous to the host target mRNA sequence, as described in WO 02/00904.

"Recombinase element" is defined herein as a genetic construct encoding a site-specific recombinase enzyme.

The term "recombinase" or "site-specific recombinase" refers to enzyme(s) that carry out SSR to alter the DNA structure. This definition includes transposases, lambda integration/excision enzymes, and site-specific recombinases. Well-known examples of recombinases can be found in Cre-lox, FLP/FRT, R/RS, Gin/gix, a pSR1 system, a cer system, and a fim system (for example, N. L. Craig, *Annu. Rev. Genet.*, 22:17 (1988); Odell et al., *Use of site-specific recombination systems in plants. Homologous Recomb. Gene Silencing Plants* (1994), pp 219-70. Paszkowski, Jerzy, ed. Kluwer: Dordrecht, Germany). Additionally, SSR systems have been identified in microorganisms such as phage, bacterium (e.g., *E. coli*), yeast and the like. This includes the *E. coli* lambda att P system for integration and excision (Zubko et al. *Nature Biotechnology* 18:442 (2000)) and the *Streptomyces* phage C31 integrase (Groth et al. *Proc. Natl. Acad. Sci. USA* 97:5995 (2000)). When the SSR system separated from these microorganisms with the use of a Cre/lox system derived from P1 phage (WO 93/01283) is introduced into organisms (including plants) different from the organism X from which this system had been derived, it behaves in the same way as in the original organism. The SSR system of yeast (*Zygosaccharomyces rouxii*) [pSR1 system; H. Matsuzaki et al., *J. Bacteriology*, 172:610 (1990)] can also be used in accordance with the present invention. This pSR1 system also maintains its inherent function in higher plants (H. Onouchi et al., *Nucleic Acid Res.*, 19: 6373 (1991)).

"Gene silencing-recombinase element" is defined herein as a genetic construct comprising a TS that can be expressed as ds RNA, to thereby trigger GS of the target gene. The gene silencing-recombinase element is a substrate for SSR, such that the timing of SSR and the activation of the promoter(s) operably linked to the TS act together to regulate expression of the TS. The SSR may involve directly repeated or inverted site-specific sequences. Optionally, the gene silencing-recombinase element may comprise introns, transcriptional 'STOP' fragments, and/or multiple copies of the TS or a promoter.

"Recombinase site" or "site-specific sequence" means a DNA sequence that a recombinase will recognize and bind to. It will be appreciated that this may be a wild type or mutant recombinase site, as long as functionality is maintained and the recombinase enzyme may still recognize the site, bind to the DNA sequence, and catalyze the recombination between two adjacent recombinase sites.

The term "floxed" will refer to the flanking of a genetic element, or a portion thereof, with tandem site-specific sequences. The site-specific sequences may be oriented in the same orientation, i.e., directly repeated (such that the DNA element is removed upon SSR), or in opposite orientations from one another (such that the DNA element is inverted upon SSR). The floxed element may be a single promoter, a transcriptional 'STOP' blocking element, a promoter operably linked to a target sequence, or a combination of these and other genetic elements.

A "site-specific recombination substrate" or "SSR substrate" refers to any DNA that is a substrate of SSR, resulting from the action of the site-specific recombinase on recombinase sites. It includes floxed DNA elements, i.e., those DNA elements flanked by recombinase sites.

"Introns" are sequences of "junk" DNA found in the middle of gene sequences in most eukaryotes. Their function is not known. These intron sequences are transcribed, but removed from within the pre-mRNA transcript before the mRNA is translated into a protein. This-process of intron removal occurs by self-splicing of the sequences (exons) on either side of the intron. It is possible to artificially "split" an intron into a 5' portion and a 3' portion (hereinafter referred to, respectively, as the "5' intron" and the "3' intron" portions). The site of "splitting" can be selected randomly, as only the terminal regions of the intron typically contain 5' and 3' splice signals that must be initially recognized and paired across the intron for excision during mRNA splicing.

"Transcription 'Stop' Fragment" or "blocking fragment" refers to nucleotide sequences that contain one or more regulatory signals, such as polyadenylation signal sequences, capable of terminating transcription. Examples include the 3' non-regulatory regions of genes encoding nopaline synthase and the small subunit of ribulose bisphosphate carboxylase. The blocking fragment blocks the transcription of a coding sequence when placed in the 5' non-translated region, i.e., between the transcription start site and the ORF of the coding sequence. DNA rearrangement by SSR, such as the rearrangement that results following excision of blocking fragment, can restore proper transcription and translation. This DNA rearrangement will be referred to herein as "unblocking". When the blocking fragment is removed from the DNA by SSR, it will be appreciated by one skilled in the art that a site-specific sequence remains which does not interfere with proper transcription and translation of the coding sequence.

"Gene silencing-mobility element" is defined herein as a genetic construct comprising a redundant target sequence ($TS_R$) under the control of a highly and constitutively expressed promoter. The gene silencing-mobility element permits generation of an effective mobile GS signal that can spread throughout the plant.

"Redundant target sequence" ($TS_R$) refers to a sequence that is homologous to both the trigger of GS (i.e., TS in ds RNA) and the target of GS (i.e., the target gene) and that is expressed under the control of a strong constitutive promoter. $TS_R$ mRNA may be identical to that of the target gene or be an incomplete or mutant version of the target mRNA that is unable to express the target gene product; $TS_R$ must, however, comprise at least TS. $TS_R$ mRNA is subject to GS and is able to maintain the mobile GS signal even when the target gene is not transcribed in the presence of its cognate TS dsRNA. In contrast, $TS_R$ is not silenced and is unable to silence the target gene in the absence of its cognate TS ds RNA.

"Gene" refers to a nucleic acid fragment that expresses mRNA, functional RNA, or specific protein, including regulatory sequences. The term "native gene" refers to a gene as found in nature. The term "chimeric gene" refers to any gene that contains: 1.) DNA sequences, including regulatory and coding sequences that are not found together in nature; or 2.) sequences encoding parts of proteins not naturally adjoined; or 3.) parts of promoters that are not naturally adjoined. Accordingly, a chimeric gene may comprise regulatory sequences and coding sequences that are derived from different sources, or comprise regulatory sequences and coding sequences derived from the same source, but arranged in a manner different from that found in nature. A "transgene" refers to a foreign gene that has been introduced into the genome by transformation and is stably maintained. Transgenes may include, for example, genes that are either heterologous or homologous to the genes of a particular organism to be transformed. Additionally, transgenes may comprise native genes inserted into a non-native organism, or chimeric genes. The term "endogenous gene" refers to a native gene in its natural location in the genome of an organism.

"Coding sequence" refers to a DNA or RNA sequence that codes for a specific amino acid sequence and excludes the non-coding sequences. The terms "open reading frame" and "ORF" refer to the amino acid sequence encoded between translation initiation and termination codons of a coding sequence. The terms "initiation codon" and "termination codon" refer to a unit of three adjacent nucleotides ('codon') in a coding sequence that specifies initiation and chain termination, respectively, of protein synthesis (mRNA translation).

"Regulatory sequences" and "suitable regulatory sequences" each refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences which may be a combination of synthetic and natural sequences. As is noted above, the term "suitable regulatory sequences" is not limited to promoters; however, some suitable regulatory sequences useful in the present invention will include (but are not limited to): constitutive plant promoters, plant tissue-specific promoters, plant developmental stage-specific promoters, inducible plant promoters and viral promoters.

The "3' region" or "3' UTR" means the 3' non-coding regulatory sequences located downstream of a coding sequence. This DNA can influence the transcription, RNA processing or stability, or translation of the associated coding sequence (e.g. for a recombinase, a transgene, etc.).

"Promoter" refers to a nucleotide sequence, usually upstream (5') to its coding sequence, which controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that are capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue-specificity of a promoter. It is capable of operating in both orientations (5' to 3' and 3' to 5'), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions.

"Constitutive promoter" refers to a promoter that directs gene expression in all tissues and at all times. "Regulated promoter" refers to a promoter that directs gene expression not constitutively but in a temporally- and/or spatially-regulated manner and includes tissue-specific, developmental stage-specific, and inducible promoters. It includes natural and synthetic sequences, as well as sequences which may be a combination of synthetic and natural sequences. Different promoters may direct the expression of a gene in different tissues or cell types, or at different stages of development, or in response to different environmental conditions. New promoters of various types useful in plant cells are constantly being discovered; numerous examples may be found in the compilation by Okamuro et al. (*Biochemistry of Plants* 15:1-82 (1989)). Since in most cases the exact boundaries of regulatory sequences have not been completely defined, DNA fragments of different lengths may have identical promoter activity. Typical regulated promoters useful in plants include, but are not limited to: safener-inducible promoters, promoters derived from the tetracycline-inducible system, promoters derived from salicylate-inducible systems, promoters derived from alcohol-inducible systems, promoters derived from glucocorticoid-inducible systems, promoters derived from pathogen-inducible systems, and promoters derived from ecdysome-inducible systems.

"Tissue-specific promoter" refers to a regulated promoter that is not expressed in all plant cells, but instead is only expressed in one or more cell types in specific organs (e.g., leaves, shoot apical meristem, flower, or seeds), specific tissues (e.g., embryo or cotyledon), or specific cell types (e.g., leaf parenchyma, pollen, egg cell, microspore- or megaspore-mother cells, or seed storage cells). These also include "developmental-stage specific promoters" that are temporally regulated, such as in early or late embryogenesis, during fruit ripening in developing seeds or fruit, in fully differentiated leaf, or at the onset of senescence. It is understood that the developmental specificity of the activation of a promoter (and, hence, of the expression of the coding sequence under its control) in a transgene may be altered with respect to its endogenous expression. For, example, when a transgene under the control of a floral promoter is transformed into a plant, even when it is the same species from which the promoter was isolated, the expression specificity of the transgene will vary in different transgenic lines due to its insertion in different locations of the chromosomes.

"Plant developmental stage-specific promoter" refers to a promoter that is expressed not constitutively but at a specific plant developmental stage(s). Plant development goes through different stages. In the context of this invention, the germline goes through different developmental stages starting, say, from fertilization through development of embryo, vegetative shoot apical meristem, floral shoot apical meristem, anther and pistil primordia, anther and pistil, micro- and macrospore mother cells, and macrospore (egg) and microspore (pollen).

"Seed-specific" promoter refers to a promoter that is expressed only in the seed.

"Synthetic anther promoter" refers to the G9/SGB6 hybrid promoter (U.S. Pat. No. 5,470,359; U.S. Pat. No. 5,837,850).

"Pollen-specific" promoters refer to promoters that are only expressed in pollen, such as LAT52 (Twell et al. *Trends in Plant Sciences* 3:305 (1998)).

"Flower" or "floral"-specific promoters refer to promoters whose expression occurs in the flower or flower primordia. They include floral common germline, male germline, and female germline promoters.

"Conditionally activating" refers to activating a recombinase that is normally not expressed. In the context of this invention, it refers to expression of recombinase either by a cross and/or by an inducer, if it is inducible.

"Expression" refers to the transcription and stable accumulation of sense (mRNA) or functional RNA. Expression may also refer to the production of protein. "Overexpression" refers to a level of expression in transgenic organisms that exceeds levels of expression in normal or untransformed organisms. "Enhanced expression" refers to expression of the target sequence over endogenous levels of expression for homologous sequences, and particularly as compared to expression in systems where the target sequence is subject to GS.

"Constitutive expression" refers to expression using a constitutive or regulated promoter. "Conditional" and "regulated expression" refer to expression controlled by a regulated promoter. "Transient expression" in the context of this invention refers to expression only in specific developmental stages or tissue in one or two generations. "Non-specific expression" refers to constitutive expression or low level, basal ('leaky') expression in nondesired cells, tissues, or generations.

"Altered levels" refers to a level of expression in transgenic organisms that differs from that of normal or untransformed organisms.

"Promoter activation" means that the promoter has become activated (or turned "on") so that it functions to drive the expression of a downstream genetic element. Constitutive promoters are continually activated. A regulated promoter may be activated by virtue of its responsiveness to various external stimuli (e.g., inducible promoter), or developmental signals during plant growth and differentiation, such as tissue specificity (e.g., floral-specific, anther-specific, pollen-specific, seed-specific, etc.) and development-stage specificity (e.g., vegetative-specific or floral-, shoot-, or apical meristem-specific, male germline-specific, female germline-specific, etc.).

"Inducible promoter" refers to those regulated promoters that can be turned "on" in one or more cell types by a stimulus external to the plant, such as a chemical, light, hormone, stress, or a pathogen.

"Operably-linked" refers to the association of nucleic acid sequences on a single nucleic acid fragment so that the function of one is affected by the other. For example, a promoter is operably-linked with a coding sequence or functional RNA when it is capable of affecting the expression of that coding sequence or functional RNA (i.e., the coding sequence or functional RNA is under the transcriptional control of the promoter). Coding sequences can be operably-linked to regulatory sequences in sense or anti-sense orientation. "Unlinked" means that the associated genetic elements are not closely associated with one another and the function of one does not affect the other.

The term "altered plant trait" means any phenotypic or genotypic change in a transgenic plant relative to the wild-type or non-transgenic plant host.

"Priming" or "enabling" refers to the removal of blocking sequences upstream of a promoter and/or gene, such that the gene can become activated in response to the appropriate environmental cue, stage of development, or presence in a specific tissue/cell type. When a genetic element is enabled or primed by the removal of a blocking fragment or inversion of a DNA construct, the promoter element may or may not be free to drive the expression of the downstream element. For example, in FIGS. 1, 2, and 3, SSR will result in inversion of the genomic DNA, thereby enabling the gene silencing-recombinase construct. However, transcription of both copies of TS will not occur until the promoter(s) is activated or induced. Thus, production of ds TS RNA will require both enabling and activating the promoter(s) driving the TS.

"Production tissue" refers to mature, harvestable tissue consisting of non-dividing, terminally-differentiated cells. It excludes young, growing tissue consisting of germline, meristematic, and non-fully-differentiated cells.

"Genetically linked" refers to physical linkage of transgenes such that they co-segregate in progeny.

"Genetically unlinked" refers to the lack of physical linkage of transgenes such that they do not co-segregate in progeny.

"Morphological trait" refers to traits of morphology, such as shoots, roots, calli, tumors, flowers, or leaves.

"Transformation" refers to the transfer of a foreign gene or sequence into the genome of a host organism. Examples of methods of plant transformation include *Agrobacterium*-mediated transformation (De Blaere et al. *Meth. Enzymol.* 143:277 (1987)) and particle-accelerated or "gene gun" transformation technology (Klein et al. *Nature* (London) 327:70-73 (1987); U.S. Pat. No. 4,945,050). The terms "transformed", "transformant" and "transgenic" refer to plants or calli that have been through the transformation process and contain a foreign gene integrated into their chromosome. The term "untransformed" refers to normal plants that have not been through the transformation process.

"Stably transformed" refers to cells that have been selected and regenerated on a selection media following transformation.

"Genetically stable" and "heritable" refer to chromosomally-integrated genetic elements that are stably maintained in the plant and stably inherited by progeny through successive generations.

"Wild-type" refers to the normal gene, virus, or organism found in nature without any known mutation.

"Genome" refers to the complete genetic material of an organism.

"Genetic trait" means a genetically determined characteristic or condition, which is transmitted from one generation to another.

"Homozygous" state means a genetic condition existing when identical alleles reside at corresponding loci on homologous chromosomes. In contrast, "heterozygous" state means a genetic condition existing when different alleles reside at corresponding loci on homologous chromosomes. A "hybrid" refers to any offspring of a cross between two genetically unlike individuals. "Inbred" or "inbred lines" or "inbred plants" means a substantially homozygous individual or variety. This results from the continued mating of closely related individuals, especially to preserve desirable traits in a stock.

The term "ortholog" or "orthologous genes" refer to genes related by common phylogenetic descent. Orthologous genes are those genes from one species that correspond to a gene in another species that is related via a common ancestral species (a homologous gene), but which has evolved to become different from the gene of the other species.

"Selfing" or "self fertilization" refers to the transfer of pollen from an anther of one plant to the stigma (a flower) of that same said plant. Selfing of a hybrid (F1) results in a second generation of plants (F2).

The term "plant life cycle" means a complete sequence of developmental events in the life of a plant, such as from fertilization to the next fertilization or from flowering in one generation to the next.

The term "generation" means a plant life cycle starting from fertilization to fertilization. The "first generation plant" is defined as the plant in which the first recombination event occurs. It includes F1 hybrid that arise by genetic crosses between two non-identical individuals, as well as plants that are induced (e.g., chemically) to express the recombinase. The "second generation plant" is the progeny of the first generation plant.

"Primary transformant" and "$T_0$ generation" refer to transgenic plants that are of the same genetic generation as the tissue which was initially transformed (i.e., not having gone through meiosis and fertilization since transformation).

"Secondary transformants" and the "$T_1$, $T_2$, $T_3$, etc. generations" refer to transgenic plants derived from primary transformants through one or more meiotic and fertilization cycles. They may be derived by self-fertilization of primary or secondary transformants or by crosses of primary or secondary transformants with other transformed or untransformed plants.

Principle of the Regulated Gene Silencing Method

The present invention provides constructs and methods for the conditional or regulated expression of gene silencing. This is possible by employing site-specific recombinases, expressed under the control of a variety of constitutive, inducible, tissue-specific or development-stage-specific promoters. The invention makes use of at least two recombinase elements. The first element is a site-specific recombinase element, encoding a site-specific recombinase under the control of plant regulatory sequences. The second element is a gene silencing-recombinase element, encoding a target sequence (TS) which must be expressed as ds RNA under the control of plant regulatory sequences. The promoters expressing the two recombinase elements are either constitutively expressed or regulated. Additionally, the promoter controlling expression of each recombinase element may be the same promoter, or different promoters but with overlapping expression profiles. The synthesis of ds TS RNA is blocked until expressed in the presence of an active recombinase.

FIG. 1 illustrates the principle of the method for regulated gene silencing, using two recombinase elements. The first element is the site-specific recombinase element (not shown), encoded by P1-R, wherein:

P1 is a first promoter; and

R is a recombinase.

The gene silencing recombinase element has the general structure of RS-$TS_{INV}$-$P2_{INV}$-RS*-$TS_{INV}$-polyA, wherein:

RS and RS* are opposingly oriented recombinase sites responsive to the recombinase (e.g., lox and lox*, wherein lox and lox* are opposingly oriented);

$TS_{INV}$ is an inverted target sequence whose orientation is from 3'-5';

$P2_{INV}$ is an inverted second promoter whose orientation is from 3'-5'; and polyA is the 3' region of a gene containing a polyadenylation signal.

P1 and $P2_{INV}$ are operably linked to their down stream elements. When P1 is activated prior to $P2_{INV}$ in the plant life cycle, expression of the recombinase will result in inversion of any element contained between the opposingly oriented recombinase sites responsive to the recombinase (i.e., inversion of $TS_{INV}$-$P2_{INV}$ to yield P2-TS), such that the modified gene silencing recombinase element comprises RS-P2-TS-RS*-$TS_{INV}$-polyA. Following activation of promoter P2, transcription of RS-P2-TS-RS*-$TS_{INV}$-polyA will lead to production of ds RNA encoding TS (ds TS RNA). This ds RNA silencing trigger will initiate gene silencing of the specific target gene having homology to TS.

A variety of different recombinase elements may be constructed and introduced into plants so as to provide for conditional GS. This permits over-expression, silencing, or modulation of expression of the specific genetic traits encoded by the target gene. By matching promoters (responsive to various inducers, plant tissues or plant developmental states), inverted or blocking fragments, and TSs, virtually any-$TS_R$ target gene's expression may be regulated at any plant development stage or in any plant generation. Each of these individual components will thus be discussed in detail below.

Recombinase Elements

The invention makes use of a variety of constructs referred to herein as recombinase elements. Each recombinase element comprises regulatory sequences required to express a gene in a cell (e.g., appropriate promoter and terminator sequences). For the purposes of the present invention, these recombinase elements can be broadly classified as site-specific recombinase elements, gene silencing-recombinase elements, or gene silencing-mobility elements.

Promoters

The present invention makes use of a variety of plant promoters to drive the expression of a site-specific recombinase, a TS within a gene silencing-recombinase element, and/or a $TS_R$ within a gene silencing-mobility element. Regulated expression of TS (and therefore formation of ds TS RNA) is possible by placing the TS and/or recombinase under the control of promoters that may be conditionally regulated. Any promoter functional in a plant will be suitable, including (but not limited to): constitutive plant promoters, plant tissue-specific promoters, plant development-stage-specific promoters, inducible plant promoters, viral promoters, male germline-specific promoters (e.g., specific to anther primordia, anther sporophyte and to pollen gametophyte), female germline-specific promoters, flower-specific promoters, and vegetative shoot apical meristem-specific promoters.

Several tissue-specific regulated genes and/or promoters have been reported in plants. These include genes encoding the seed storage proteins (e.g., napin, cruciferin, β-conglycinin, and phaseolin), zein or oil body proteins (e.g., oleosin), genes involved in fatty acid biosynthesis (e.g., acyl carrier protein, stearoyl-ACP desaturase, and fatty acid desaturases (fad 2-1)), and other genes expressed during embryo development (e.g., Bce4 [see, for example: EP 255378 and Kridl et al., *Seed Science Research* 1:209-219 (1991)]). Particularly useful for seed-specific expression is the pea vicilin promoter (Czako et al., *Mol. Gen. Genet.* 235(1): 33-40 (1992)). Other useful promoters for expression in mature leaves are those that are switched on at the onset of senescence, such as the SAG promoter from Arabidopsis (Gan et al., *Science (Washington, D.C.)* 270 (5244): 1986-8 (1995)).

A class of fruit-specific promoters expressed at or during anthesis through fruit development, at least until the beginning of ripening, is discussed in U.S. Pat. No. 4,943,674, the disclosure of which is hereby incorporated by reference. cDNA clones that are preferentially expressed in cotton fiber have been isolated (John et al., *Proc. Natl. Acad. Sci. U.S.A.* 89(13): 5769-73 (1992)). Also, cDNA clones from tomato displaying differential expression during fruit development have been isolated and characterized (Mansson et al., *Mol. Gen. Genet.* 200:356-361 (1985); Slater et al., *Plant Mol. Biol.* 5:137-147 (1985)). The promoter for polygalacturonase gene is active in fruit ripening. The polygalacturonase gene is described in U.S. Pat. No. 4,535,060, U.S. Pat. No.

4,769,061, U.S. Pat. No. 4,801,590, and U.S. Pat. No. 5,107,065, whose disclosures are incorporated herein by reference.

Mature plastid mRNA for psbA (one of the components of photosystem II) reaches its highest level late in fruit development, in contrast to plastid mRNAs for other components of photosystem I and II which decline to nondetectable levels in chromoplasts after the onset of ripening (Piechulla et al., *Plant Mol. Biol.* 7: 367-376 (1986)). Recently, cDNA clones representing genes apparently involved in tomato pollen (McCormick et al., *Tomato Biotechnology* (1987) Alan R. Liss: New York) and pistil (Gasser et al., *Plant Cell* 1:15-24 (1989)) interactions have also been isolated and characterized.

Other examples of tissue-specific promoters include those that direct expression in leaf cells following damage to the leaf (e.g., from chewing insects), in tubers (e.g., patatin gene promoter), and in fiber cells (an example of a developmentally-regulated fiber cell protein is E6 [John et al., *Proc. Natl. Acad. Sci. U.S.A.,* 89(13): 5769-73 (1992)]). The E6 gene is most active in fiber, although low levels of transcripts are found in leaf, ovule and flower.

The tissue-specificity of some "tissue-specific" promoters may not be absolute and may be tested by one skilled in the art using the diphtheria toxin sequence. One can also achieve tissue-specific expression with "leaky" expression by a combination of different tissue-specific promoters (Beals et al., *Plant Cell,* 9:1527-1545 (1997)). Other tissue-specific promoters can be isolated by one skilled in the art (see U.S. Pat. No. 5,589,379).

Germline-specific promoters, responsive to male-, female-, or both male-female-specific cell lineages are also useful in the present invention. For instance, transgenes can be expressed from pollen by site-specific recombinase expression under the control of male germline-specific genes in anther primordia genes (e.g., *Arabidopsis* Apetala 3 and *Pistilata* (PI) or their orthologs from other plant species), in sporophytic anther tissue (e.g., Bcp I and TA29 promoters) or gametophytic pollen. Similarly, transgenes can be expressed from ovules by site-specific recombinase expression under the control of female germline-specific genes in ovule primordia. Transgenes can be expressed from both male- and female-specific germlines by expression of an active site-specific recombinase gene under the control of promoters for genes common to both male and female lineages in flower (e.g., *Arabidopsis agamous* gene or its orthologs in other species), in floral meristem (e.g., *Arabidopsis* Apetala 1, Leafy, and Erecta or their orthologs from other species), and in vegetative shoot apical meristem (e.g., *Arabidopsis* WUSCHEL (WUS) and SHOOT MERISTEMLESS (STM) or their orthologs from other species). Promoters of shoot apical meristem are especially useful for expressing transformation marker genes early in tissue-culture following selection or in planta following a transformation phenotype.

Similarly, several inducible promoters ("gene switches") have been reported. Many are described in the reviews by Gatz (*Current Opinion in Biotechnology,* 7:168-172 (1996); *Annu. Rev. Plant Physiol. Plant Mol. Biol.* 48: 89-108 (1997)). These include the tetracycline repressor system, the Lac repressor system, copper-inducible systems, salicylate-inducible systems (e.g., the PR1a system), and glucocorticoid- (Aoyama T. et al., *N—H Plant Journal* 11:605-612 (1997)) and ecdysome-inducible systems. Also included are the benzene sulphonamide- (U.S. Pat. No. 5,364,780) and alcohol- (WO 97/06269 and WO 97/06268) inducible systems and glutathione S-transferase promoters. Other studies have focused on genes inducibly regulated in response to environmental stress or stimuli such as increased salinity, drought, pathogen, and wounding (Graham et al., *J. Biol. Chem.* 260:6555-6560 (1985); Graham et al., *J. Biol. Chem.* 260:6561-6554 (1985); Smith et al., *Planta* 168:94-100 (1986)). Accumulation of a metallocarboxypeptidase-inhibitor protein has been reported in leaves of wounded potato plants (Graham et al., *Biochem. Biophys. Res. Comm.* 101: 1164-1170 (1981)). Other plant genes that have been reported to be induced include methyl jasmonate, elicitors, heat-shock, anerobic stress, or herbicide safeners.

Site-Specific Recombinase Systems

The present invention provides site-specific recombinase systems for use in regulated gene silencing.

A SSR system consists of two elements: 1) an enzyme (i.e., recombinase) that binds to the DNA sequence specifically and catalyzes the recombination between DNA sequences if two or more of the sequences exist; and 2) recombination sites having a characteristic DNA sequence. When the two site-specific sequences are oriented in the same direction at a given interval on the same DNA molecule, the region held by these DNA sequences is excised from the DNA molecule, such as a plasmid, chromosome or the like. When the two DNA sequences are oriented in opposite directions on the same DNA molecule, the region held by these DNA sequences is inverted.

The site-specific sequences and their cognate recombinase enzymes can be from any natural SSR system. Well-known examples include Cre-lox, FLP/FRT, R/RS, Gin/gix, a pSR1 system, a cer system, and a fim system (for example, N. L. Craig, *Annu Rev. Genet.,* 22:17 (1988); Odell et al., *Use of site-specific recombination systems in plants. Homologous Recomb. Gene Silencing Plants* (1994), pp 219-70. Paszkowski, Jerzy, ed. Kluwer: Dordrecht, Germany). Additionally, SSR systems have been identified in microorganisms such as phage, bacterium (e.g., *E. coli*), yeast and the like. When the SSR system separated from these microorganisms with the use of a Cre/lox system derived from P1 phage (WO 93/01283) is introduced into organisms (including plants) different from the organism from which this system had been derived, it behaves in the same way as in the original organism. The SSR system of yeast (*Zygosaccharomyces rouxii*) (known as the pSR1 system; H. Matsuzaki et al., *J. Bacteriology,* 172: 610 (1990)) can also be used in accordance with the present invention. This pSR1 system also maintains its inherent function in higher plants (H. Onouchi et al., *Nucleic Acid Res.,* 19: 6373 (1991)).

Since the levels of the recombinase enzyme required are not expected to be high, several "specific" promoters can be used that may otherwise be too weak to express the gene of interest. Furthermore, since SSR depends on a threshold level of the recombinase, there may be a tolerance for leaky transcription that results in sub-threshold levels of recombinase.

Furthermore, increased "tissue-selectivity" to available regulated promoters is provided by decreasing the efficiency of wild-type Cre-mediated recombination, thereby raising the threshold of recombinase required by using either a mutant site for SSR and/or a mutant recombinase that is not proficient in recombination. Such mutants are well known, at least for the Cre-lox system. The Applicants have shown previously that when using safener-inducible Cre expression to activate the expression of a transgene (35S:luciferase), the use of a mutant lox site (lox72) and a wild type lox P site in Cre-mediated activation of the transgene reduces the basal activity of the promoter compared to using both wild type lox P sites (Yadav et al., WO 01/36595 A2; WO 00/17365 A2; EP1115870 A2).

The non-specificity of recombinase expression can be further reduced (i.e., its expression specificity further increased) by other post-transcriptional approaches including: 1) using a chimeric recombinase gene that is poorly translated (e.g., having a non-ideal context sequence around the initiation codon following Kozak's rule; or having additional short ORFs in the 5' untranslated region, as in yeast GCN4 mRNA; or having 3' UTR sequences that make mRNA unstable; or 2) using a mutant recombinase that has less cellular stability (i.e., shorter half-life). Such mutants could be made by adding PEST sequences (Sekhar et al., *Jrl. Receptor Signal Transduction Res.* 18 (2-3): 113-132 (1998)).

Once a system is developed in a given crop, it can be easily adapted for conditional expression of a variety of target genes.

Gene Silencing-Recombinase Elements

In addition to recombinase elements, the present invention also utilizes gene silencing-recombinase elements. Each gene silencing-recombinase construct comprises a floxed portion of DNA, wherein the floxed DNA may consist essentially of a promoter, a blocking fragment in the form of a Transcriptional 'STOP' fragment, a TS, an intron (or a portion thereof), or any combination of these elements. The gene silencing-recombinase construct becomes functional according to a variety of factors, two of which involve the position and choice of promoter (as discussed above). The remaining elements which may optionally be present in the gene silencing-recombinase construct are discussed individually below.

Target Sequences

The TS of the present invention: 1.) comprise partial or complete sequence(s) of a target gene whose silencing is desired; and 2.) are capable of forming hairpin RNA or ds RNA to silence the target gene and, optionally, the redundant target gene ($TS_R$).

In one embodiment, TSs may comprise the partial or entire sequence of endogenous genes encoding proteins of the GS apparatus itself, allowing higher expression of any transgene without limitation from its own GS. Such host genes involved in GS include, but are not limited to: qde-1, qde-2, qde-3, rde-1, rde-2, rde-3, rde-4, mut-2, mut-7, ego-1, AGO1, SGS-2/SDE-1, SGS-1, SGS-3, RdRP, and Dicer.

In alternative embodiments, TSs of the present invention may include partial or complete sequences of: 1.) endogenous genes involved in cell wall biosynthesis (e.g., for integrated corn bio-refinery) or development (e.g., flowering); or 2.) transgenes encoding a repressor of a trait gene, to thereby result in indirect induction of the trait gene (infra) (e.g., biotic or abiotic resistance).

Floxed Target Sequences and/or Floxed Blocking Fragments and/or Floxed Promoters Target sequences of the present invention are typically included within a floxed DNA fragment or juxtaposed next to a floxed DNA fragment. As a result of this operable linkage within the gene silencing-recombinase element, transcription of the target sequence is unable to produce a gene silencing phenotype (e.g., a ds TS RNA molecule), until TS expression is "activated". DNA rearrangement by SSR will occur only when an active recombinase enzyme is present in the cell, thereby enabling proper transcription of the target sequence to result in activation of gene silencing by formation of ds RNA. The DNA rearrangement either inverts the floxed DNA fragment (in the case of inverted site-specific recombinase sites) or physically removes the floxed fragment from the DNA leaving only a single site-specific recombinase sequence (in the case of directly repeated site-specific recombinase sites). In either case, upon promoter activation within the gene silencing-recombinase construct, the TS is then transcribed to result in a ds RNA of the TS. This can be achieved by: 1.) transcription of a single mRNA that forms a ds RNA; or 2.) transcription of complementary mRNAs, for example by the activity of two promoters transcribing the same TS. If an intron is present in the product, this is removed by mRNA splicing. All gene silencing-recombinase elements yield ds RNA, which then serves as the "trigger" to activate gene silencing of the target gene.

It will be recognized by a person having ordinary skill in the art that it is also possible to incorporate a variety of other DNA elements within the floxed DNA fragments which do not interfere with the functionality described above. These extraneous elements may either be rendered irrelevant to expression of TS following DNA inversion, or be removed from the genome in a controlled manner according to activation of the recombinase enzyme. Modifications of this variety are thus included within the scope of this invention.

Introns

The presence of introns are not required, per se, in the present invention. However, since inverted sequences are unstable in genomes (especially bacterial genomes), introns permit maintenance of inverted sequences in the genome by physically separating the sequences. Intron splicing can then result in inverted TS.

As is well known in the art, introns are typically considered as sequences of "junk" DNA found in the middle of gene sequences and whose function is not currently appreciated. The majority of plant protein-coding genes contain introns, which must be removed from pre-mRNAs prior to the production of mRNA for translation into protein. These intron sequences of DNA are transcribed, but they are removed from within the pre-mRNA transcript by splicing together the sequences (exons) on either side of the intron. This splicing reaction enables production of an active protein, while the intron sequence is excised.

Splicing of introns is thought to proceed via an "intron definition" mechanism, in which the 5' and 3' splice signals are initially recognized and paired across the intron. Thus, it is possible to artifically split an intron into a 5' and 3' portion without significantly altering the 5' and 3' terminal ends of the intron where splice signals are typically located.

Plant Hosts

The present invention additionally provides plant hosts for transformation with the present recombinase elements. Moreover, the host plant for use in the present invention is not particularly limited. Examples of herbaceous plants used as the host plant include: tobacco (*Tabacum* sp.), tomato (*Lycopersicom* sp.), castor (*Ricinus* sp.), potato (*Solanum* sp.), carrot (*Dacus* sp.), oilseed rape (*Brassica* sp.), sunflower (*Helianthus* sp.), sugar beet (*Beta*), sugarcane (*Saccharium* sp.), cotton (*Gossypium* sp.), arabidopsis (*Arabidopsis* sp.), alfalfa (*Medicago* sp.), peas (*Pisum* sp.), soybean (*Glycine* sp.), rice (*Oryza* sp.), corn (*Zea* sp.), rye (*Secale* sp.), poplar (*Populus* sp.), and spruce (*Picea*).

Examples of arboreous plants used as the host plant include: poplar (*Populus*), eucalypti (*Eucalyptus*), acacia (*Acacia*), pear (*Pyrus*), apple (*Malus*), grape (*Vitis*), walnut (*Juglans*), plum (*Prunus*), rose (*Rosa*), and spruce (*Picea*). However, the host plants for use in the present invention are not limited thereto.

Plant Transformation

One skilled in the art recognizes that the expression level and regulation of a transgene in a plant can vary significantly from line to line. Thus, one has to test several lines to find one with the desired expression level and regulation. Once a line is identified with the desired regulation specificity of a site-specific recombinase element, it can be crossed with lines carrying a gene silencing-recombinase element for production of ds TS RNA.

A variety of techniques are available and known to those skilled in the art for introduction of constructs into a plant cell host. These techniques include transformation with DNA employing *A. tumefaciens* or *A. rhizogenes* as the transforming agent, electroporation, particle acceleration, etc. (see, for example, EP 295959 and EP 138341). It is particularly preferred to use the binary type vectors of Ti and Ri plasmids of *Agrobacterium* spp. Ti-derived vectors transform a wide variety of higher plants, including monocotyledonous and dicotyledonous plants, such as soybean, cotton, rape, tobacco, and rice (Pacciolti et al. *Bio/Technology* 3:241 (1985); Byrne et al. *Plant Cell, Tissue and Organ Culture* 8:3 (1987); Sukhapinda et al. *Plant Mol. Biol.* 8:209-216 (1987); Lorz et al. *Mol. Gen. Genet.* 199:178 (1985); Potrykus *Mol. Gen. Genet.* 199:183 (1985); Park et al., *J. Plant Biol.*, 38(4):365-71 (1995); Hiei et al., *Plant J.*, 6:271-282 (1994)). The use of T-DNA to transform plant cells has received extensive study and is amply described (EP 120516; Hoekema, In: *The Binary Plant Vector System*, Offset-drukkerij Kanters B. V.; Alblasserdam (1985), Chapter V; Knauf, et al., *Genetic Analysis of Host Range Expression by Agrobacterium*. In: *Molecular Genetics of the Bacteria-Plant Interaction*, Puhler, A. ed., Springer-Verlag: New York, 1983, p 245; and An, et al., *EMBO J.* 4:277-284 (1985)). For introduction into plants, the chimeric constructs of the invention can be inserted into binary vectors as described in the Examples.

Other transformation methods are available-to those skilled in the art, such as direct uptake of foreign DNA constructs (see EP 295959), techniques of electroporation (see Fromm et al. *Nature* (London) 319:791 (1986)) or high-velocity ballistic bombardment with metal particles coated with the nucleic acid constructs (see Kline et al. *Nature* (London) 327:70 (1987), and U.S. Pat. No. 4,945, 050). Once transformed, the cells can be regenerated by those skilled in the art. Of particular relevance are the recently described methods to transform foreign genes into commercially important crops, such as rapeseed (De Block et al. *Plant Physiol.* 91:694-701 (1989)), sunflower (Everett et al. *Bio/Technology* 5:1201 (1987)), soybean (McCabe et al. *Bio/Technology* 6:923 (1988); Hinchee et al. *Bio/Technology* 6:915 (1988); Chee et al. *Plant Physiol.* 91:1212-1218 (1989); Christou et al. *Proc. Natl. Acad. Sci USA* 86:7500-7504 (1989); EP 301749), rice (Hiei et al., *Plant J.*, 6:271-282 (1994)), and corn (Gordon-Kamm et al. *Plant Cell* 2:603-618 (1990); Fromm et al. *Biotechnology* 8:833-839 (1990)).

Transgenic plant cells are then placed in an appropriate selective medium for selection of transgenic cells that are then grown to callus. Shoots are grown from callus and plantlets generated from the shoot by growing in rooting medium. The various constructs normally will be joined to a marker for selection in plant cells. Conveniently, the marker may be resistance to a biocide (particularly an antibiotic such as kanamycin, G418, bleomycin, hygromycin, chloramphenicol, herbicide, or the like). The particular marker used will allow for selection of transformed cells as compared to cells lacking the DNA that has been introduced. Components of DNA constructs including transcription cassettes of this invention may be prepared from sequences which are native (endogenous) or foreign (exogenous) to the host. By "foreign" it is meant that the sequence is not found in the wild-type host into which the construct is introduced. Heterologous constructs will contain at least one region that is not native to the gene from which the transcription-initiation-region is derived.

To confirm the presence of the transgenes in transgenic cells and plants, a Southern blot analysis can be performed using methods known to those skilled in the art. Expression products of the transgenes can be detected in any of a variety of ways, depending upon the nature of the product, and include Western blots and enzyme assays. One particularly useful way to quantitate protein expression and to detect replication in different plant tissues is to use a reporter gene, such as GUS. Once transgenic plants have been obtained, they may be grown to produce plant-tissues or parts having the desired phenotype. The plant tissue or plant parts may be harvested, and/or the seed collected. The seed may serve as a source for growing additional plants with tissues or parts having the desired characteristics.

DESCRIPTION OF THE PREFERRED EMBODIMENTS

Due to the inherent capabilities of a SSR system, whereby DNA contained between two recombination sites can be either inverted or excised depending on the orientation of the recombination sites with respect to one another, the SSR strategy used for regulation of gene silencing can be embodied based on recombinase-based inversion or recombinase-based excision. Each of these strategies will be discussed below in much greater detail.

Schematic Representation of Recombinase-based Inversion and Recombinase-Based Excision as a Mechanism to Control Gene Silencing Although the present embodiments of the invention are illustrated using a Cre-Lox SSR, system, this is not intended to be limiting to the Applicants. Specifically, one skilled in the art will recognize that the present invention is applicable with any known site-specific recombinase enzyme(s) that can carry out SSR and alter the DNA structure. Thus, this includes transposases, lambda integration/excision enzymes, as well as site-specific recombinases (e.g., Cre-lox, FLP/FRT, R/RS, Gin/gix, a pSR1 system, a cer system, a fim system, the *E. coli* lambda att P system, and the *Streptomyces* phage C31 integrase).

Likewise, the only limitation concerning the site-specific sequence is that it must be recognized by the recombinase enzyme. Thus, the sequence may encode a wild type or mutant recombinase site, as long as functionality is maintained and the recombinase enzyme may still recognize the site, bind to the DNA sequence, and catalyze recombination of the floxed DNA fragment contained between two adjacent recombinase sites.

Recombinase-Based Inversion for Gene Silencing

A series of three embodiments of the invention are illustrated, based on recombinase-based inversion methodology as a technique to regulate gene silencing. For each of the schemes discussed, the following abbreviations apply:

P1 is a promoter driving the expression of the recombinase;

P2 and P3 are promoters driving the expression of TS;

TS is a target sequence;

Lox is a Lox P site containing a site-specific sequence which is recognized by the Cre recombinase enzyme;

Lox* is identical to Lox (defined above), however the orientation of the site-specific sequence is inverted with respect to Lox;

polyA is the 3' region of a gene encoding a polyadenylation signal; and ds TS RNA is double-stranded RNA encoding the target sequence (TS).

In all cases, the subscript "INV" indicates that the particular element (e.g., the promoter ($P2_{INV}$, $P3_{INV}$) or the target sequence ($TS_{INV}$)) is in an inverted orientation, such that the sequence is read in a 3' to 5' orientation. When the subscript "INV" is not present, the promoter (P2, P3) or the target sequence (TS) is oriented as 5' to 3'.

FIG. 1 was discussed previously, as illustrative of the principle of the invention for regulated gene silencing. Again, the first element is the site-specific recombinase element (not shown), which is transcribed and translated to produce a functional Cre recombinase enzyme, according to activation of a P1 promoter. The generic structure for this first element is P1-R, although many modifications could be envisioned to this basic structure.

The gene silencing-recombinase element of FIG. 1 has the general structure of lox-$TS_{INV}$-$P2_{INV}$-lox*-$TS_{INV}$-polyA Production of ds TS RNA does not occur by the gene silencing-recombinase element alone. Instead, expression of the gene silencing-recombinase element requires activation and expression of the site-specific recombinase element, which permits synthesis of a functional Cre recombinase enzyme. This enzyme is then able to recognize the site-specific recombinase Lox and Lox* sequences, in order to cause inversion of the DNA between the tandem sites (i.e., "Cre-based inversion"). Thus, the lox-$TS_{INV}$-$P2_{INV}$-lox* elements are inverted to yield a construct containing lox-P2-TS-lox*. Upon activation of the P2 promoter, the lox-P2-TS-lox*-$TS_{INV}$-polyA construct is transcribed as mRNA containing TS as an inverted duplicated sequence, the first TS in a 5' to 3' orientation, the second TS in a 3' to 5' orientation, and both separated by a Lox* site. Complying with the laws of thermodynamics, these duplicate RNA sequences will then associate according to Watson-Crick type base pairing to form a loop of ds RNA, since this conformation possesses lower free energy. With the formation of ds TS RNA, the gene silencing mechanism is triggered, leading to silencing of TS and any genes homologous to this specific sequence in the plant. The Lox* site does not interfere with this reaction.

FIGS. 2 and 3 are variations upon the general methodology presented in FIG. 1. FIG. 2 again contains a site-specific recombinase element (not shown), which is transcribed and translated to produce a functional Cre recombinase enzyme. The gene silencing-recombinase element has the general structure of lox-5' intron-$TS_{INV}$-$P2_{INV}$-lox*-3' intron-$TS_{INV}$-polyA. Again, production of ds TS RNA does not occur by the gene silencing-recombinase element alone. Instead, expression of the gene silencing-recombinase element requires activation and expression of the site-specific recombinase element, which permits synthesis of a functional Cre recombinase enzyme and inversion of the DNA between the tandem lox sites (i.e., "Cre-based inversion"). This produces a modified gene silencing-recombinase construct comprising lox-P2-TS-5' intron-lox*-3' intron-$TS_{INV}$-polyA. Transcription occurs according to activation of the P2 promoter, to produce an unspliced mRNA precursor which undergoes a normal mRNA splicing reaction, since the 34 base pair lox sequence separating the 5' and 3' portion of the intron sequence does not interfere with splicing. This results in the formation of inverted duplicated sequence (ds TS RNA), the first TS in a 5' to 3' orientation and the second TS in a 3' to 5' orientation. In contrast to FIG. 1, however, the duplicate copies of TS are not separated by a lox* site; instead, the ds TS RNA possesses a splicing junction (represented as "J" in FIG. 2). The ds TS RNA serves as the trigger for gene silencing of target gene.

In FIG. 3, the gene silencing-recombinase element is simplified, such that only P2 is floxed (i.e., lox-$P2_{INV}$-lox*-TS-$P3_{INV}$). Following Cre-based inversion of the floxed DNA, activation of the P2 and $P3_{INV}$ promoters will enable transcription of TS by both P2 and $P3_{INV}$, thus producing two copies of the TS in the mRNA. The P2 and P3 promoters are either the same or different from one another, but must possess an overlapping expression profile. The TS sequence may optionally contain poly A regions at the 3' end of the complementary DNA strands such that the TS transcript is polyadenylated. The latter is expected to enhance post-transcriptional gene silencing. Following the production of TS as inverted duplicated sequence (ds TS RNA), these sequences will associate as ds TS RNA, and enable activation of the gene silencing mechanism. This particular scheme for gene silencing is considered to be particularly useful, as it requires one to clone only a single copy of the target sequence (while TS must be cloned in both orientations in the methods described as FIGS. 1 and 2).

Recombinase-Based Excision for Gene Silencing

A series of two schemes for gene silencing are presented below based on recombinase-based excision methodology. Abbreviations and subscript definitions are the same as those used during the discussion of recombinase-based inversion.

Figure 4:
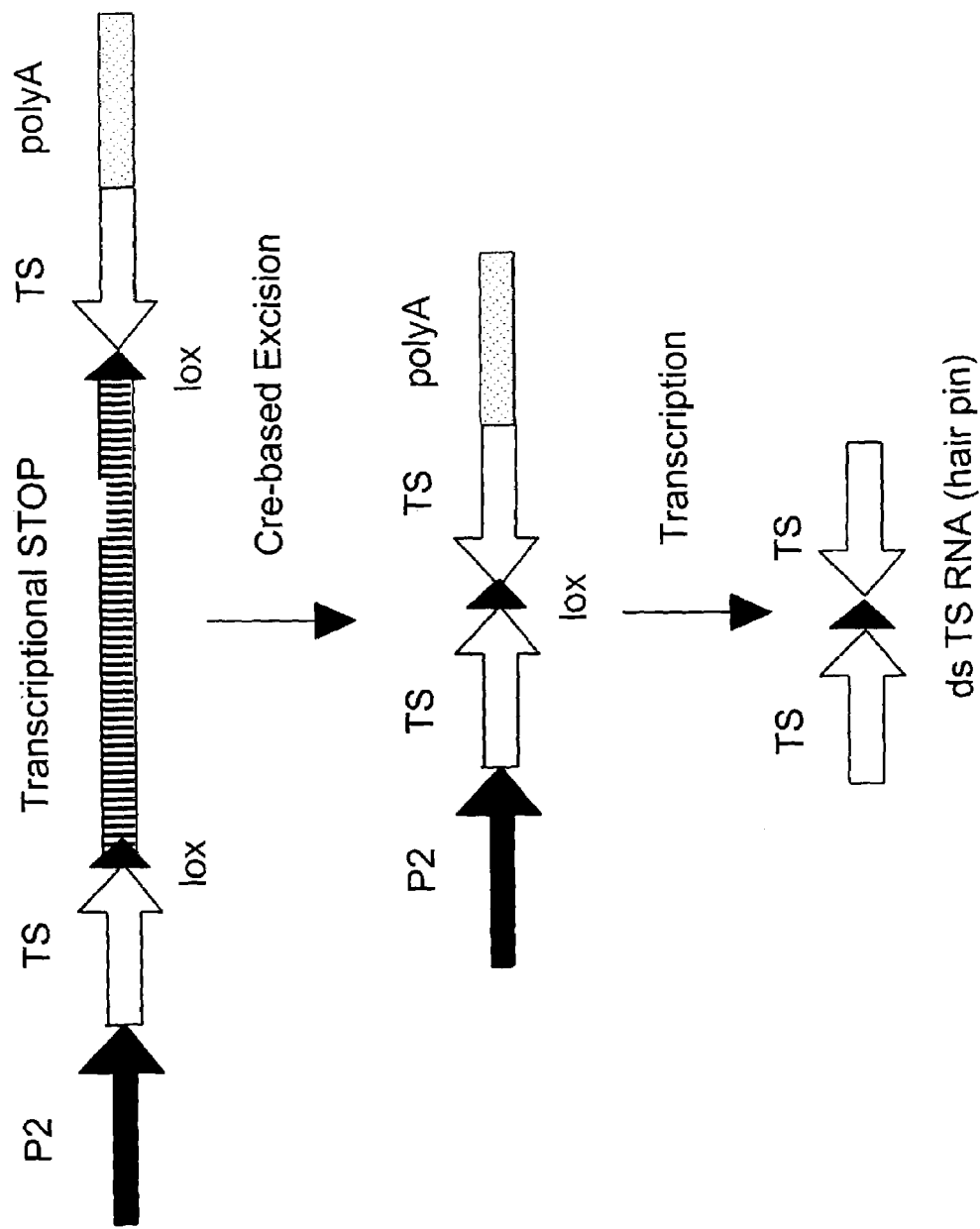
FIG. 4 shows excision of a transcriptional 'STOP' fragment by sitespecific recombination to produce ds TS RNA.
Figure 5:
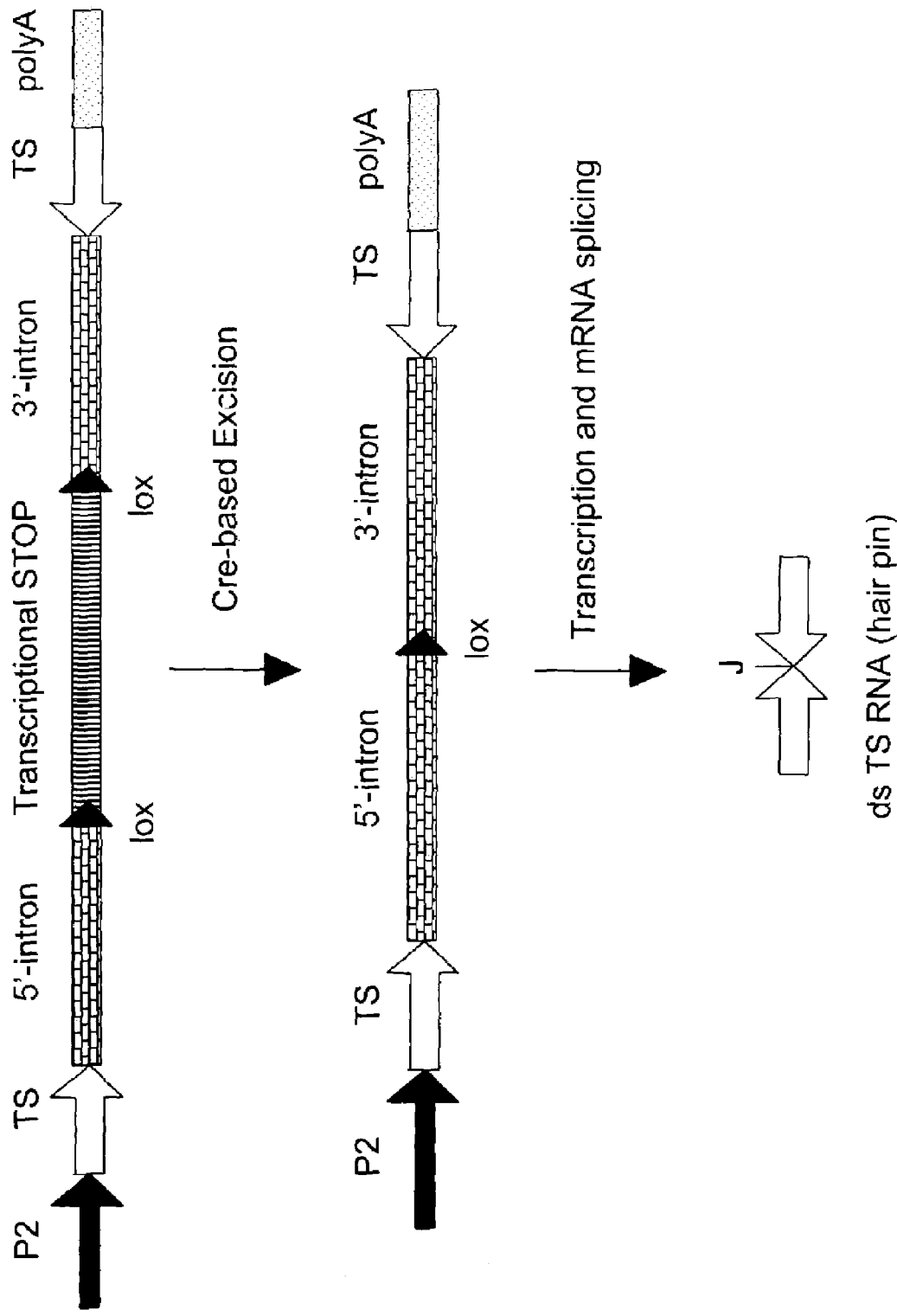
FIG. 5 shows excision of a transcriptional 'STOP' fragment by sitespecific recombination, followed by mRNA splicing of an intron to produce ds TS RNA.

The gene silencing scheme illustrated in FIG. 4 requires two recombinase elements, the first being a site-specific recombinase element (e.g., P1-R; not shown). The second component of the system is a gene silencing-recombinase element having the general structure of P2-TS-lox-Transcriptional STOP-lox-$TS_{INV}$-polyA. Again, production of ds TS RNA does not occur by the gene silencing-recombinase element alone, due to the presence of the Transcriptional STOP fragment blocking transcription of $TS_{INV}$. Instead, expression of the gene silencing-recombinase element requires activation and expression of the site-specific recombinase element, which permits synthesis of a functional Cre recombinase enzyme. This enzyme is then able to recognize the site-specific recombinase lox sequences, in order to cause excision of the floxed DNA between the tandem sites (i.e., "Cre-based excision", the effect of which causes removal of the Transcriptional STOP). This excision process leaves a modified gene silencing-recombinase element composed of P2-TS-lox-$TS_{INV}$-polyA. Upon activation of the P2 promoter, the construct is transcribed as mRNA that has an inverted duplicated sequence (dsTS RNA), the first TS in a 5' to 3' orientation and the second TS in a 3' to 5' orientation. The duplicate copies of TS are separated by a 34 bp lox site. Free energy minimization will require these-duplicate RNA sequences to associate as a loop of ds TS RNA, which can then act as a trigger for the native gene silencing mechanisms of the cell.

FIG. 5 illustrates another method for the regulation of gene silencing based on recombinase-based excision. In this case, the gene silencing-recombinase element has the general structure of P2-TS-5' intron-lox-Transcriptional STOP-lox-3' intron-$TS_{INV}$-polyA. Again, production of ds TS RNA does not occur by the gene silencing-recombinase element alone, due to the presence of the Transcriptional STOP fragment blocking transcription of $TS_{INV}$. However, upon formation of active Cre recombinase enzyme, excision of the floxed DNA occurs, thereby removing the Transcriptional STOP. Thus, the modified gene silencing-recombinase element comprises P2-TS-5' intron-lox-3' intron-$TS_{INV}$-polyA. Following activation of the P2 promoter, transcription will produce a mRNA precursor containing two copies of the TS, the first in a 5' to 3' orientation and the second in a 3' to 5' orientation. The normal mRNA splicing reaction excises the intron sequence (the 34 bp lox sequence separating the 5' and 3' portion of the intron does not interfere with splicing signal sequences and thus does not interfere with the reaction) to result in the formation of inverted duplicated sequence (dsTS RNA), the first TS in a 5' to 3' orientation and the second TS in a 3' to 5' orientation. Unlike the final ds TS RNA construct in FIG. 4 which possesses a lox site between the duplicate TS, the ds TS RNA of this embodiment instead possesses a splicing junction (represented by "J"). The ds RNA hairpin serves as the trigger for gene silencing of the target gene.

Activation of Target Sequence Expression as Double-Stranded TS RNA

The present gene silencing methodology based on SSR permits control of gene silencing within a specific tissue, developmental stage, or generation of the plant. Highly regulated control is possible by controlling: 1.) expression of the site-specific recombinase enzyme in cells containing the gene silencing-recombinase element; and 2.) transcription of TS.

The first level of regulation maintains conditionality to SSR by either: 1.) regulating recombinase enzyme expression by selection of the enzyme's operably linked promoter (e.g., P1 as a chemically inducible promoter, a tissue-specific promoter, or a developmentally-regulated promoter); or 2.) maintaining the site-specific recombinase element in a separate line, and genetically crossing the line capable of expressing the cognate recombinase to a line carrying the recombination sites and TS only when desired. This results in production of a functional recombinase in the presence of its cognate gene-silencing recombinase element. The latter is more amenable for hybrid crops. Chemical application on seeds or during germination is likely to overcome the chemical's cost and problems with its biokinetics into target cells. When chemically-induced, one or both of the recombinase elements can be under the control of a chemically inducible promoter. Chemical application can also be done in the prior generation by using a relay of two or more SSR systems (WO 01/36595 A2).

The second level of regulation for the present gene silencing system is controlled by the choice of promoter that the target sequence is operably linked to. P2 (and optionally P3), controlling expression of TS, could be selected from any constitutive, inducible, tissue-specific or developmental stage-specific promoter suitable for expression in plants. Additionally, the optional P3 promoter can be the same or different from P2, as long as both promoters possess overlapping expression profiles.

Despite the choice of either recombinase-based inversion or recombinase-based excision for regulation of gene silencing, all of the constructs embodied in the present invention can be readily transformed and tested for functionality. First, these constructs can be synthesized with a reporter target gene (e.g., luciferase or GFP) and co-introduced into cultured cells or into protoplasts by transfection, electroporation, or PEG transformation. The constructs can also be cloned into a binary vector and then tested for gene silencing by agroinfiltration into host plant leaf. Finally, the constructs can be tested transgenically.

Conditional Down-Regulation of the Gene Silencing Apparatus itself

While the general methodology of the present invention can be applied to silence any endogenous gene or transgene, it is of particular interest to obtain conditional down-regulation of one or more target genes encoding proteins of the gene silencing apparatus itself. This would allow higher expression of any transgene, without limitation from normal gene silencing. Preferred host genes to silence are therefore any host genes involved in gene silencing.

Abundant research has been performed using genetic screens in Neurospora, C. elegans, and Arabidopsis to identify genes that appear to be crucial for PTGS and RNAi. In Neurospora, qde-1, qde-2 and qde-3 (named for the "quelling-deficient" phenotype they invoke when mutated) have been found to be required for PTGS. In C. elegans, rde-1, rde-2, rde-3, rde-4 ("rde" stands for "RNAi deficient"), mut-2, mut-7 ("mut" stands for mutator) and ego-1 ("ego" stands for "enhancer of glp-1") have been identified as important for RNAi. And, in Arabidopsis thaliana, AGO1 ("AGO" stands for "argonaute"), SGS-2/SDE-1 ("SGS" stands for suppressor of gene silencing), SGS-1, and SGS-3 are known to be required for PTGS. Since many of these genes are homologs of one another, it is clear that the underlying mechanism of PTGS in these disparate organisms is similar. Further homology is observed between the Neurospora qde-1 gene, the SDE-1/SGS-2 gene of Arabidopsis, the C. elegans ego-1 gene, and a tomato gene encoding a RNA-dependent RNA polymerase (RdRP). The role of RdRP in PTGS and RNAi, respectively, is unclear; however, it is reasonable to expect that regulation of this gene could also serve to control gene silencing.

The nuclease DICER (Ambros, V. Science 293:811-813 (Aug. 3, 2001); Hutvagner, G., et al. Science 293:834-838 (Aug. 3, 2001); Knight, S. W., and B. L. Bass. Science 293: 2269-2271 (Sep. 21, 2001)) has also been implicated to play a role in gene silencing. The highly conserved gene is responsible for cleaving large ds RNA precursors into small temporal RNAs (stRNAs) and short interfering RNAs (siRNAs), which play roles in gene inactivation by RNA interference and the control of gene expression during development, respectively. It is hypothesized that these two separate phenomenom are actually different facets of one diversified system for RNA-mediated gene regulation, and thus DICER could be a useful enzyme for regulation of gene silencing.

Each of the genes mentioned above is highly conserved in evolution, suggesting that they play an important role and that their loss or down-regulation is expected to be detrimental, at least in the long run. In fact, mutations in many of these genes result in abnormal growth and development (Vance, V. and H. Vaucheret. Science 292:2277 (2001)). Furthermore, since gene silencing is involved in viral resistance, a shutdown or slowdown of the gene silencing machinery is likely to enhance viral susceptibility in those plants. Thus, regulated silencing or partial silencing of these genes in a desired tissue, stage of growth, or generation would be of great utility. It will be obvious to one skilled in the art that the present invention is readily adaptable to these purposes.

Conditional and Systemic Gene Silencing

As discussed above, SSR-based GS can be made conditional by a genetic cross that brings together the recombinase gene from one parent and the inactive silencing locus (i.e., the gene silencing-recombinase element) from the other. Alternatively, it can be made conditional by chemical treatment which induces recombinase expression under the control of a promoter responsive to the chemical. In either case, however, it is possible that SSR would not occur in all cells of the plant; thus, a plant chimera would result where not all cells would be expressing the hairpin mRNA. In order to ensure more robust silencing in the whole plant, especially in such a chimeric plant, one skilled in the art can make an effective, mobile (systemic) GS signal that provides for systemic gene silencing.

A mobile GS signal depends on both a strong silencing signal (e.g., a hairpin mRNA) and the transcriptionally active target gene, since it has been observed in both *C. elegans* and plants that transcription of the target gene is essential for generating the mobile signal. One way to generate an effective mobile GS signal is to introduce a redundant target gene ($TS_R$), which is a chimeric gene in which a complete, incomplete, or mutant sequence of the target gene (comprising at least the complete TS or $TS_{INV}$) is under the control of a highly and constitutively expressed promoter, such that it can maintain the silencing signal [once induced locally] in all tissues (even in the absence of a transcriptionally active target gene). In this specific embodiment, the plant would necessarily require the following genetic elements:

A) a first recombinase element having the general structure P1-R;
B) a second gene silencing-recombinase element having a general structure selected from the group consisting of:
  1) RS-P2$_{INV}$-RS*-TS-P3$_{INV}$;
  2) RS-TS$_{INV}$-P2$_{INV}$-RS*-TS$_{INV}$-polyA;
  3) RS-5' Intron-TS$_{INV}$-P2$_{INV}$-RS*-3' Intron-TS$_{INV}$-polyA;
  4) P2-TS-RS-STP-RS-TS$_{INV}$-polyA; or
  5) P2-TS-5' Intron-RS-STP-RS-3' Intron-TS$_{INV}$-polyA; and
C) a third gene silencing-mobility element having a general structure of P4-TS$_R$;
wherein:
  a) P1 is a first promoter that is chemically inducible;
  b) R is a recombinase;
  c) RS and RS* are opposingly oriented recombinase sites responsive to the recombinase;
  d) P2 and P3 are second and third promoters that have overlapping expression profiles and are either the same or different;
  e) P2$_{INV}$ is an inverted second promoter whose orientation is from 3'-5';
  f) TS is a target sequence optionally having an operably-linked poly A region at the 3' end of each complementary strand;
  g) TS$_{INV}$ is an inverted target sequence whose orientation is from 3'-5';
  h) 5'Intron is the N-terminal portion of an intron;
i) 3'Intron is the C-terminal portion of an intron;
j) STP is a Transcriptional 'STOP' fragment;
k) polyA is the 3' region of a gene;
l) P4 is strong constitutive promoter; and
m) $TS_R$ is a redundant target gene comprising at least a target sequence selected from the group consisting of TS and $TS_{INV}$;

wherein P1, P2, $P2_{INV}$, optionally P3, and P4 are operably linked to their down stream elements.

Following the chemical induction of the P1 promoter, the recombinase would be expressed, causing the inversion or excision of the elements between the recombinase sites on the second gene silencing-recombinase element and thereby permitting the formation of ds-RNA encoding the TS. The TS would be silenced throughout the plant due to systemic GS, as a result of the constitutive expression of the third genetic element (i.e., P4-$TS_R$). Thus, the result of this strategy is silencing of the native target gene when the native gene is turned on.

The above strategy will also be useful to induce silencing in the majority of the plant when only a limited portion of the plant is treated. This is important because chemically-induced expression of almost all commercially important traits should occur either constitutively or at developmental stages post-germination. However, for cost reasons, the preferred method of chemical application (instead of foliar application in the field) is typically via treatment of either: 1.) seeds before planting (pre-treatment); or 2.) roots of hydrophonic plants. Thus, it would be desirable to utilize a strategy to chemically-induce a signaling response (i.e., systemic GS) that would persist even in the absence of the chemical inducer. Thus, chemical pretreament of seed can result in robust, conditional 'knockout' of a target gene at any development stage of a plant.

Finally, if systemic GS signal is not inherited, it provides for chemical induction of SSR in somatic tissues (but not in the germline), thus providing heritability to chemical induction in subsequent generations.

For purposes of clarity, it is important to note that although the same methodology is utilized according to the disclosure herein, the conditional 'knockout' or silencing of a target gene can produce drastically different results in terms of gene expression, depending on the particular gene which is targeted for silencing. Specifically, GS would occur when utilizing a chemically-inducible hairpin transcript, as taught by the present invention, directed against the target gene to trigger the target gene's own systemic GS. In contrast, trait gene over-expression could indirectly result when the target gene encodes a repressor of a trait gene, since GS of the repressor will indirectly induce the trait gene. Of course, it will be obvious to one skilled in the art that the present methodology based on SSR would not necessarily be required to promote trait gene over-expression by GS of a repressor, in cases where the chemically-inducible expression of the hairpin transcript is sufficient.

The approaches described above for systemic GS can readily be taken by those of skill in the art.

EXAMPLES

The present invention is further defined in the following Examples. These Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual;* Cold Spring Harbor Laboratory: Cold Spring Harbor, N.Y. (1989) (Maniatis); by T. J. Silhavy, M. L. Bennan, and Enquist, L. W. Experiments with Gene Fusions, Cold Spring Harbor Laboratory: Cold Spring Harbor, N.Y. (1984); and by Ausubel, F. M. et al., Current Protocols in Molecular Biology, published by Greene Publishing Assoc. and Wiley-Interscience (1987).

Restriction enzyme digestions, phosphorylations, ligations and transformations were done as described in Sambrook, J. et al., supra. Restriction enzymes were obtained from New England Biolabs (Boston, Mass.), GIBCO/BRL (Gaithersburg, Md.), or Promega (Madison, Wis.). Taq polymerase was obtained from Perkin Elmer (Branchburg, N.J.). Growth media was obtained from GIBCO/BRL (Gaithersburg, Md.).

All PCR reactions were performed in a 50 µl reaction volume, composed of: 1 µl template DNA (5 ng), 1 µl primer #1 (100 pmol), 1 µl primer #2 (100 pmol), 5 µl 10× PWO buffer, 2 µl dNTPs, 39 µl water, and 1 µl PWO enzyme (Roche Molecular Biochemicals, Indianapolis, Ind.). Cycle conditions were: 95° C. for 5 min; 30 cyles of 95° C. for 1 min, 57° C. for 1 min, and 72° C. for 90 sec; 72° C. for 7 min; and 4° C., hold.

The meaning of abbreviations is as follows: "sec" means second(s), "min" means minute(s), "h" means hour(s), "d" means day(s), "µL" means microliter(s), "mL" means milliliter(s), "L" means liter(s), "µM" means micromolar, "mM" means millimolar, "M" means molar, "mmol" means millimole(s), "µmole" mean micromole(s), "g" means gram(s), "µg" means microgram(s), "ng" means nanogram(s), "U" means units, "bp" means base pairs, and "kB" means kilobase(s).

Example 1

Promoter Inversion Construct

This Example describes the construction of a gene silencing-recombinase construct, having the general structure of lox-P2$_{INV}$-lox*-TS-P3$_{INV}$, embodied as LoxP:35S promoter: LoxP: Luc: Actin 2 promoter. This construct corresponds with the schematic shown as FIG. 3.

Specifically, a promoter inversion construct was made in which the TS (i.e., Luc) is flanked by two promoters (i.e., 35S and Actin 2). Of these two promoters, the 35S promoter is flanked by Lox P sites, such that its orientation is changed by SSR from being divergent with respect to the other promoter (inactive silencing construct) to being convergent (active silencing construct).

A LoxP:35S promoter:LoxP: Luc: Actin 2 promoter (complement) was made by PCR as follows: Plasmid pGV751 (WO 00/17365A2), which contains 35S promoter: Lox P:blocking fragment:Lox P: firefly luciferase:3' ocs, was used as the DNA template for PCR products 1 and 2. A 1025 bp PCR product 1 containing the 35S promoter and Lox P [nucleotides 41-1062 of final construct, see below] was made using SEQ ID NO: 1 (P314 upper primer) and SEQ ID NO:2 (P315 lower primer). A 708 bp PCR product 2 containing the 5' end of the firefly luciferase ORF [nucleotides 1033-1740 of final contruct below] was made using SEQ ID NO: 3 (P316 upper primer) and SEQ ID NO: 4 (P317 lower primer).

A 1246 bp PCR product 3 containing the Arabidopsis thaliana actin 2 promoter [nucleotides 1712-2957 of final contruct below] was made using SEQ ID NO: 5 (P318 upper primer) and SEQ ID NO: 6 (P319 lower primer) on pSK (Stratagene) containing the promoter region.

A 1733 bp PCR 1+2 product was made by mixing PCR products 1 and 2 and subjecting the mixture to PCR using the outer primers P314 upper primer and P317 lower primer. A 1680 bp Hind III-Xma I fragment as the resulting PCR product was isolated and cloned in pSK, resulting in plasmid pGV954.

A 1235 bp Xma I-Sac I fragment isolated from PCR product 3 was cloned into pGV954, digested with Xma I and Sac I, to result in plasmid pGV955.

In order to insert the Lox P site in front of the 35S promoter in pGV955, first a 991 bp PCR product 4 was made using SEQ ID NO: 7 (P330 upper primer) and SEQ ID NO: 8 (P320 lower primer) on plasmid pGV751 DNA template. A 458 bp Sal I-Nsi I fragment from PCR product 4 was isolated and cloned into pGV955, digested with Sal I-Nsi I. The resultant plasmid, pGV956, was confirmed by DNA sequencing.

Thus, plasmid pGV956 contains 2957 bp of a gene silencing-recombinase element that is comprised of (5' to 3'):

6 bp (nucleotides 1-6) Sal I site;
  34 bp (nucleotides 7-40) Lox P site, 5'-ATA ACT TCG TAT AGC ATA CAT TAT ACG AAG TTA T-3' (SEQ ID NO: 9);
  6 bp (nucleotides 41-46) Hind III site;
  951 bp (nucleotides 47-997) 35S promoter similar to nucleotides 3505 to 4455 in cloning vector PKANNIBAL [Genbank Accession No. AJ311873; Wesley, V. S., et al. Plant J. 27(6):581-590 (2001)];
  34 bp (nucleotides 998-1031) Lox P* sequence (opposite orientation with respect to the first Lox P site), 5'-ATA ACT TCG TAT AAT GTA TGC TAT ACG AAG TTA T-3' (SEQ ID NO: 10);
  25 bp (nucleotides 1032-1057) polylinker sequence, 5'-GAA TTC TGC AGG ATC CTG ACT AGT C-3' (SEQ ID NO: 11);
  664 bp partial Luc ORF encoding N-terminal residues corresponding to nucleotides 45-708 in pSK-Luc (Promega) [Genbank Accession No. U47122, Cloning vector pSP-luc+, Luciferase cassette vector, complete sequence];
  15 bp (nucleotides 1721-1735) polylinker sequence, 5'-CCC GGG TAC CTA GGC-3' (SEQ ID NO: 12);
  1214 bp (nucleotides 1736-2949) Arabidopsis thaliana actin 2 (ACT2) promoter corresponding to nucleotides 1-1214 of Genbank Accession No. U41998; An, Y. Q., et al. Plant J. 10(1):107-121 (1996)); and
  8 bp (nucleotides 2950-2957) Linker sequence (Sac I), 5'-CCG AGC TC-3'.

The following sites may be used to replace the first (35S) promoter, second (Act2) promoter, and the TS (Luc): Hind III-Xho I sites for the first promoter; Xma I and Sac I sites for the second promoter; and Bam HI-Xma I for the TS. The TS may be a transcribed region or a promoter region of the target gene. If it is the former, it may additionally be flanked by 3' UTR sequences, i.e., Lox: P2$_{INV}$:Lox:first 3'UTR (complement):TS:second 3'UTR: P3$_{INV}$.

The 2957 bp Sal I-Sac I fragment from pGV956 containing the entire silencing construct described above will be isolated and cloned into pBin19 binary vector ([Frisch, D. A. et al., Plant Mol. Biol. 27(2):405-409 (1995) (Genbank Accession No. U09365)]), cut with Sal I-Sac I. The resultant binary plasmid, pBE956, will be transformed into Cre-expressing E. coli to isolate a clone (pBE9561) that has undergone Cre-mediated inversion. Binary plasmids pBE956 and pBE956I will be transformed into Agrobacterium and transformed into an Arabidopsis transgenic line carrying 35S:Luciferase. The transgenic 35S:luciferase expression is expected to be silenced upon Cre-mediated SSR.

Example 2

Promoter Plus Target Sequence Inversion Construct

This Example describes the construction of an active gene silencing-recombinase construct, having the general structure of lox-P2-TS-5' intron-lox*-3' intron-TS$_{INV}$-polyA, embodied as LoxP:35S promoter: Luc ORF:5' intron:LoxP*: 3' intron:Luc ORF$_{INV}$: 3' OCS UTR. This construct corresponds with the schematic shown as FIG. 2. Synthesis of the active silencing construct occurred as follows:

A 991 bp PCR product 6 containing the 35S promoter was made by using SEQ ID NO: 1 (P314 upper primer) and SEQ ID NO: 8 (P320 lower primer) on plasmid pGV751 DNA template [WO 00/1 7365A2, described in Example 1]. A 968 bp Hind III-Bam HI fragment from PCR product 6 was cloned into pSK+ (Stratagene) to result in plasmid pGV957.

A 748 bp PCR product 7 containing a 3' ocs was made by using SEQ ID NO: 3 (P316 upper primer) and SEQ ID NO: 13 (P321 lower primer) on plasmid pGV751 DNA template. A 726 bp Xba I-Sac I fragment from PCR product 7 was isolated and cloned into pGV957, digested with Xba I-Sac I, to result in pGV958.

A 713 bp PCR product 8 containing the partial (5') firefly luciferase ORF was made using SEQ ID NO: 3 (P316 upper primer) and SEQ ID NO: 13 (P321 lower primer) on plasmid pGV751 DNA template.

A 156 bp PCR product 9a containing the 5' end of the STS intron (potato gene, Genbank Accession No. X04753 M25351) was made using SEQ ID NO: 14 (P322 upper primer) and SEQ ID NO: 15 (P323 lower primer) on plasmid containing the intron sequence as DNA template. Additionally, 124 bp PCR product 9b containing the 3' end of the STS intron was made using SEQ ID NO: 16 (P324 upper primer) and SEQ ID NO: 17 (P325 lower primer). Together, a 256 bp PCR product 9 was made using SEQ ID NO: 14 (P322 upper primer) and SEQ ID NO: 16 (P324 lower primer) on a mixture of PCR products 9a and 9b as DNA template. It contains the entire intron sequence with a Lox P site separating the 5' and 3' portions of the intron.

A 704 bp PCR product 10 containing the complement of the partial (5') firefly luciferase ORF was made using SEQ ID NO: 18 (P326 upper primer) and SEQ ID NO: 19 (P327 lower primer) on plasmid pGV751 DNA template.

A 939 bp PCR product 8+9 was made using SEQ ID NO: 3 (P316 upper primer) and SEQ ID NO: 16 (P324 lower primer) on a mixture of PCR products 8 and 9 as DNA template. A 908 bp Bam HI-Avr II fragment from PCR product 8+9 and a 681 bp Avr II-Xba I fragment from PCR product 10 were isolated and cloned together between Bam HI and Xba I of pGV958 to result in pGV964.

Thus, plasmid pGV964 contains 3327 bp of an active gene silencing-recombinase element that is comprised of (5' to 3'):

- 6 bp (nucleotides 1-6) Sal I site;
- 34 bp (nucleotides 7-40) Lox P site, 5'-ATA ACT TCG TAT AGC ATA CAT TAT ACG AAG TTA T-3' (SEQ ID NO: 9);
- 6 bp (nucleotides 41-46) Hind III site;
- 951 bp (nucleotides 47-997) 35S promoter similar to nucleotides 3505 to 4455 in cloning vector pKANNIBAL [Genbank accession No. AJ311873; Wesley, V. S., et al. *Plant J.* 27 (6):581-590 (2001)];
- 24 bp (nucleotides 998-1021) polylinker sequence, 5'-GAA TTC TGC AGG ATC CTG ACT AGT-3' (SEQ ID NO: 20);
- 665 bp (nucleotides 1022-1686) partial Luc ORF encoding N-terminal residues corresponding to nucleotides 45-708 in pSK-Luc (Promega) [Genbank Accession No. U47122, Cloning vector pSP-luc+, Luciferase cassette vector, complete sequence];
- 7 bp (nucleotides 1687-1693) polylinker sequence, 5'-CCC GGGT-3';
- 115 bp (nucleotides 1694-1808) of potato ST-LS1 gene containing 5' end of intron no. 2 [corresponding to nucleotides 2645-2759 of Genbank Accession No. X04753 M25351; Eckes, P., et al. *Mol. Gen. Genet.* 205:14-22 (1986)];
- 34 bp (nucleotides 1809-1842) Lox P* sequence (opposite orientation with respect to the first Lox P site), 5'-ATA ACT TCG TAT AAT GTA TGC TAT ACG AAG TTA T-3' (SEQ ID NO: 10);
- 77 bp (nucleotides 1843-1919) of modified potato ST-LS1 gene containing 3' end of intron no 2 [corresponding to nucleotides 2760-2836 Genbank Accession No. X04753 M25351; Eckes, P., et al., supra except that the last four bases of the intron sequence herein (5'-CCAG-3') are different from the published sequence of 5'-TTAG-3'];
- 10 bp (nucleotides 1920-1929), 5'-GTTACCCGGG-3' (SEQ ID NO: 21);
- 664 bp (nucleotides 1930-2593), complement of the partial Luc ORF (i.e. in opposite orientation with respect to the Luc ORF above) encoding N-terminal residues corresponding to nucleotides 45-708 in pSK-Luc (Promega) [Genbank Accession No. U47122, Cloning vector pSP-luc+, Luciferase cassette vector, complete sequence];
- 2 bp (nucleotides 2594-2595), 5'-GG-3';
- 724 bp (nucleotides 2596-3319), 3' ocs corresponding to nucleotides 5279-6002 pkannibal vector [Genbank Accession No. AJ311873; Wesley, V. S., et al. *Plant J.* 27(6):581-590 (2001)]; and
- 8 bp (nucleotides 3320-3327) Linker sequence (Sac I), 5'-TTG AGC TC-3'.

The following sites may be used to replace the promoter (35S), TS (luc), and 3' UTR (OCS): Hind III-Bam HI sites for the promoter; and Bam HI and Xba I for the TS (TS:5' intron: Lox P: 3' intron: TS (complement)).The TS may be a transcribed region or a promoter region of the target gene, and Xba I-Sac I for 3' UTR.

An inactive silencing construct will be made from the above by Cre-mediated inversion either in vitro or in *E. coli* carrying the Cre gene. This will result in an inactive gene silencing-recombinase construct, having the general structure of lox-5' intron$_{INV}$-TS$_{INV}$ P2$_{INV}$-lox*-3' intron-TS$_{INV}$-polyA, embodied as Lox P-5' intron$_{INV}$-LUC ORF$_{INV}$-35S promoter$_{INV}$-Lox P*-3' intron-Luc ORF$_{INV}$-3' OCS UTR. This construct corresponds with the schematic shown as FIG. 2. This inactive silencing construct is inverted upon SSR to result in the active silencing construct in which a transgene is transcribed to result in a ds TS RNA.

The gene silencing-recombinase element will be introduced into a binary vector and the resultant binary vector will be transformed into *Agrobacterium*. Following this transformation, the *Agrobacterium* will be used to transform an *Arabidopsis* transgenic line carrying 35S:Luciferase. The transgenic 35S:luciferase expression is expected to be silenced upon Cre-mediated SSR.

What is claimed is:

1. A gene silencing site-specific recombination system comprising:
   a) a first recombinase element having the general structure P1-R, wherein P1 is a first promoter and R is a recombinase coding sequence and 3' region; and
   b) a second recombinase element having the general structure: RS-X-RS*-Y wherein:
   i) RS and RS* are opposingly oriented recombinase sites responsive to the recombinase;
   ii) X is a nucleic acid fragment comprising at least one second promoter in a 3' to 5' orientation, wherein X comprises 5' Intron-TSINV-P2INV; and
   iii) Y is a nucleic acid fragment comprising 3' Intron-TSINV-polyA;

wherein:
   1) P2INV comprises an inverted second promoter whose orientation is from 3'-5';
   2) TSINV is an inverted target sequence whose orientation is from 3'-5', and is complementary to a sequence in the coding region of a target gene;
   3) polyA is the 3' region of a gene;
   4) 5' Intron is the N-terminal portion of an intron; and,
   5) 3' Intron is the C-terminal portion of said intron; wherein, when said system is present in a plant cell comprising the target gene, expression of the recombinase results in inversion of X, yielding a recombined second recombinase element, RS-P2-TS-5' Intron-RS*-3' Intron-TSINV-polyA, wherein transcription of TS and TSINV by P2 results in the production of double-stranded RNA that causes silencing of the target gene.

2. The gene silencing site-specific recombination system according to claim 1 wherein the recombinase and recombinase site are selected from the group consisting of Cre-lox, FLP/FRT, R/RS, and Gin/gix.

3. The gene silencing site-specific recombination system according to claim 1 wherein the first promoter and at least one second promoter are selected from the group consisting of
   a) constitutive plant promoters;
   b) plant tissue-specific promoters;
   c) plant development stage-specific promoters;
   d) chemically-inducible plant promoters; and
   e) viral promoters.

4. A gene silencing site-specific recombination system comprising:
   a) a first recombinase element having the general structure P1-R, wherein P1 is a first promoter and R is a recombinase coding sequence and 3' region; and
   b) a second recombinase element having the general structure RS-5' Intron-TSINV-P2INV-RS*-3' Intron-TSINV-polyA, wherein:
   i) RS and RS* are opposingly oriented recombinase sites responsive to the recombinase;
   ii) 5' Intron is the N-terminal portion of an intron;
   iii) TSINV is an inverted target sequence and whose orientation is from 3'-5', and is complementary to a sequence in the coding region of a target gene;
   iv) P2INV is an inverted second promoter whose orientation is from 3'-5';
   v) 3'Intron is the C-terminal portion of said intron; and
   vi) polyA is the 3' region of a gene;
   wherein, when the system is present in a plant cell comprising the target gene, recombinase expression results in recombination of the second recombinase element to yield RS-P2-TS-5' Intron-RS*-3' Intron-TSINV-polyA, wherein P1 and P2 are operably linked to their down stream elements, wherein following transcription of the recombined second recombinase element, the intron is excised by mRNA splicing and the transcripts of TS and TSINV hybridize to form a double-stranded RNA that causes silencing of the target gene.

5. The gene silencing site-specific recombination system according to claim 4 wherein the first promoter is a germline promoter.

6. The gene silencing site-specific recombination system according to claim 5 wherein the germline promoter is selected from the group consisting of:
   male germline-specific promoters;
   female germline-specific promoters;
   common germline-specific promoters;
   floral common germline-specific promoters;
   vegetative shoot apical meristem-specific promoters; and
   floral shoot apical meristem-specific promoters.

7. The gene silencing site-specific recombination system according to claim 6 wherein the male germline-specific promoter is derived from genes selected from the group consisting of genes specific to anther primordia, anther sporophyte and pollen gametophyte.

8. The gene silencing site-specific recombination system according to claim 6 wherein the common germline-specific promoter is derived from genes selected from the group consisting of Apetala 3 (AP3), Pistillata (Pl), synthetic anther promoter, TA29, BCP1 and orthologs thereof.

9. The gene silencing site-specific recombination system according to claim 6 wherein the common germline-specific promoter is derived from genes selected from the group consisting of Leafy (LFY), Apetala 3 (AP3), Pistillata (Pl), Apetala 1 (AP1), Agamous (AG), Pistillata (Pl) and orthologs thereof.

10. The gene silencing site-specific recombination system according to claim 6 wherein the floral common germline-specific promoter is derived from genes selected from the group consisting of Agamous (AG), Apetala 1 (AP1), Apetala 3 (AP3), Leafy (LFY) and orthologs thereof.

11. The gene silencing site-specific recombination system according to claim 6 wherein the vegetative shoot apical meristem-specific promoter is selected from the group consisting of Agamous (AG), Apetala 1 (AP1), Apetala 3 (AP3), Leafy (LFY), Aintegumenta (ANT), Clavata 3 (CLV3), Wushel (WUS), Meristemless (STM) and orthologs thereof.

12. The gene silencing site-specific recombination system according to claim 4 wherein the second promoter is selected from the group consisting of:
a) constitutive plant promoters;
b) plant tissue-specific promoters;
c) plant development stage-specific promoters;
d) chemically-inducible plant promoters; and
e) viral promoters.

13. The gene silencing site-specific recombination system according to claim 1 or claim 4 wherein the target sequence silences a target gene selected from the group consisting of:
a) a gene encoding an enzyme of a biosynthetic pathway;
b) a gene encoding a storage protein;
c) a gene conveying sterility;
d) a gene conveying a specific phenotype on a plant or plant cell;
e) a hormone biosynthetic gene; and
f) a gene involved in gene silencing.

14. The gene silencing site-specific recombination system according to claim 13 wherein the genes involved in gene silencing are selected from the group consisting of:
a) qde-1, qde-2, and qde-3;
b) rde-1, rde-2, rde-3, and rde-4;
c) mut-2, and mut-7;
d) ego-1;
e) AGO1;
f) SGS-2/SDE-1, SGS-1, and SGS-3;
g) RdRP; and,
h) Dicer.

15. The gene silencing site-specific recombination system according to claim 4 wherein the recombinase coding sequences and recombinase site are selected from the group consisting of Cre-lox, FLP/FRT, R/RS, and Gin/gix.

16. The gene silencing site-specific recombination system according to claim 4 wherein the first recombinase element and the second recombinase element may be genetically linked or unlinked.

17. The gene silencing site-specific recombination system according to claim 16 wherein the first recombinase element and the second recombinase element are genetically unlinked.

* * * * *